(12) United States Patent
Ritz et al.

(10) Patent No.: US 10,842,487 B2
(45) Date of Patent: Nov. 24, 2020

(54) METHOD AND APPARATUS FOR LOADING AND IMPLANTING A SHAPE MEMORY IMPLANT

(71) Applicant: BioMedical Enterprises, Inc., San Antonio, TX (US)

(72) Inventors: Joseph P. Ritz, Castroville, TX (US); Daniel F. Cheney, San Antonio, TX (US); Adam T. Knight, San Antonio, TX (US)

(73) Assignee: BioMedical Enterprises, Inc., San Antonio, TX (US)

( * ) Notice: Subject to any disclaimer, the term of this patent is extended or adjusted under 35 U.S.C. 154(b) by 291 days.

(21) Appl. No.: 15/844,133

(22) Filed: Dec. 15, 2017

(65) Prior Publication Data

US 2019/0117219 A1  Apr. 25, 2019

Related U.S. Application Data

(60) Provisional application No. 62/574,845, filed on Oct. 20, 2017.

(51) Int. Cl.
*A61B 17/068* (2006.01)
*A61B 17/10* (2006.01)
(Continued)

(52) U.S. Cl.
CPC ...... *A61B 17/0682* (2013.01); *A61B 17/0642* (2013.01); *A61B 17/0644* (2013.01);
(Continued)

(58) Field of Classification Search
CPC . A61B 17/10; A61B 17/0642; A61B 17/0644; A61B 17/0682;
(Continued)

(56) References Cited

U.S. PATENT DOCUMENTS

| 1,106,241 A | 8/1914 | Richardson |
| 2,544,492 A | 3/1947 | Downing |

(Continued)

FOREIGN PATENT DOCUMENTS

| EP | 0682920 A1 | 2/1995 |
| EP | 0857462 A1 | 1/1998 |

(Continued)

OTHER PUBLICATIONS

4-Fusion Shape Memory Implant Training Slide Images, Memometal, Inc., 2008.
(Continued)

*Primary Examiner* — Thanh K Truong
*Assistant Examiner* — David G Shutty
(74) *Attorney, Agent, or Firm* — Christopher L. Makay

(57) ABSTRACT

An implant insertion device is designed for use with a shape memory implant movable between an unconstrained shape and an insertion shape. The implant insertion device maintains the shape memory implant in its insertion shape until the delivery of the shape memory implant into tissue or bone. Upon the release of the shape memory implant from the implant insertion device, the shape memory implant attempts to move from its insertion shape to its unconstrained shape, thereby releasing mechanical energy into the tissue or bone.

17 Claims, 28 Drawing Sheets

(51) Int. Cl.
*A61B 17/064* (2006.01)
*A61B 17/00* (2006.01)

(52) U.S. Cl.
CPC .... *A61B 17/10* (2013.01); *A61B 2017/00867* (2013.01); *A61B 2017/0641* (2013.01); *A61B 2017/0645* (2013.01)

(58) Field of Classification Search
CPC .. A61B 2017/00867; A61B 2017/0642; A61B 2017/0682; A61B 2017/0684
See application file for complete search history.

(56) References Cited

U.S. PATENT DOCUMENTS

| | | | |
|---|---|---|---|
| 3,939,828 | A | 2/1976 | Mohr et al. |
| 4,438,769 | A | 3/1984 | Pratt et al. |
| 4,485,816 | A | 12/1984 | Krumme |
| 4,665,906 | A | 5/1987 | Jervis |
| 4,869,243 | A | 9/1989 | Huene |
| 5,067,957 | A | 11/1991 | Jervis |
| 5,171,252 | A | 12/1992 | Friedland |
| 5,246,443 | A | 9/1993 | Mai |
| 5,779,707 | A | 7/1998 | Bertholet et al. |
| 5,785,713 | A | 7/1998 | Jobe |
| 6,001,110 | A | 12/1999 | Adams |
| 6,268,589 | B1 | 7/2001 | Flot |
| 6,323,461 | B2 | 11/2001 | Flot |
| 6,412,639 | B1 | 7/2002 | Hickey |
| 6,607,542 | B1 | 8/2003 | Wild |
| 6,685,708 | B2 | 2/2004 | Monassevitch et al. |
| 6,783,531 | B2 | 8/2004 | Allen |
| 7,240,677 | B2 | 7/2007 | Fox |
| 7,344,539 | B2 | 3/2008 | Serhan et al. |
| 7,556,647 | B2 | 7/2009 | Drews et al. |
| 8,118,952 | B2 | 2/2012 | Gall et al. |
| 8,137,351 | B2 | 3/2012 | Prandi |
| 8,191,220 | B2 | 6/2012 | Magnuson et al. |
| 8,211,109 | B2 | 7/2012 | Groiso |
| 8,584,853 | B2 | 11/2013 | Knight et al. |
| 8,596,514 | B2 | 12/2013 | Miller et al. |
| 9,072,610 | B2 * | 7/2015 | Zalenski ............... A61F 2/4611 |
| 9,585,656 | B2 * | 3/2017 | Taber ................. A61B 17/0642 |
| 2005/0043757 | A1 | 2/2005 | Arad et al. |
| 2005/0009660 | A1 | 5/2005 | Allen |
| 2005/0107807 | A1 | 5/2005 | Nakao |
| 2005/0143749 | A1 | 6/2005 | Zalenski et al. |
| 2009/0062800 | A1 | 3/2009 | Shano |
| 2009/0272786 | A1 | 11/2009 | Zeiner et al. |
| 2010/0133316 | A1 | 6/2010 | Lizee et al. |
| 2012/0024937 | A1 | 2/2012 | Allen |
| 2012/0085809 | A1 | 4/2012 | Milo |
| 2012/0209305 | A1 | 8/2012 | Deodhar et al. |
| 2013/0026206 | A1 | 1/2013 | Fox |
| 2013/0026207 | A1 | 1/2013 | Fox |
| 2013/0030437 | A1 | 1/2013 | Fox |
| 2013/0030438 | A1 | 1/2013 | Fox |
| 2013/0231667 | A1 | 9/2013 | Taylor et al. |
| 2014/0018809 | A1 | 1/2014 | Allen |
| 2014/0097228 | A1 | 4/2014 | Taylor et al. |
| 2014/0277516 | A1 | 9/2014 | Miller et al. |
| 2015/0257801 | A1 | 9/2015 | Palmer et al. |
| 2016/0066907 | A1 * | 3/2016 | Cheney ............ A61B 17/0642 606/75 |
| 2016/0074037 | A1 * | 3/2016 | Cheney ............ A61B 17/0684 227/175.1 |
| 2017/0000482 | A1 * | 1/2017 | Averous ............ A61B 17/0642 |
| 2017/0281157 | A1 * | 10/2017 | Hartdegen ......... A61B 17/8052 |
| 2019/0046183 | A1 * | 2/2019 | Hartdegen ......... A61B 17/0644 |

FOREIGN PATENT DOCUMENTS

| | | |
|---|---|---|
| EP | 0826340 A2 | 3/1998 |
| EP | 1870042 A1 | 12/2007 |
| FR | 2874166 A1 | 2/2006 |
| WO | 1992017122 A2 | 10/1992 |
| WO | 2008129061 A1 | 10/2008 |
| WO | 20100004330 A1 | 1/2010 |
| WO | 2013055824 A1 | 4/2013 |

OTHER PUBLICATIONS

4-Fusion Shape Memory Implant Brochure, Memometal, Inc., Jun. 23, 2009.

MemoGraph Brochure, M.B.A. (Memory Biological Application), Parc Club de Nancy de Brabois,Batiment B11, 4 allee Vincennes, 54500 Vandceurve, France, 1999.

OSStaple Brochure Including pictures of staple loaded in shipping block, BioMedical Enterprises, Inc., 14875 Omicron Drive, Suite 205, San Antonio, TX 78245, 2010.

E. A. Van Amerongen et al., "Four-Corner Arthrodesis Using the Quad Memory Staple," Journal of Hand Surgery (European vol. 2008) (Jan. 7, 2009).

J. Rethnam et al., "Mechanical Characteristics of Three Staples Commonly Used in Foot Surgery," Journal of Foot and Ankle Research (Feb. 25, 2009) available at http://www.jfootankleres.com/content/2/1/5.

T. F. Smith, "The Bone Staple: Tried and True Superhero of Bone Fixation," Educational Materials Update Chapter 41 (2010) available at www.podiatryinstitute.com/pdfs/Update 2010/2010 41.pdf.

Elevest Procedure Kit, Instructions for Use by CooperSurgical (© 2007).

Agee WristJack, Surgeon's Manual by Hand BioMechanics Labs, Inc. (© 1990-2002).

Development of a Nickel-Titanium Shape Memory Alloy Bone Repair Staple and Other In-Vivo Orthopaedic and Cardio-Vascular Devices, A.W. Anson, D.H.R. Jenkins, and S. Andrews, Proceedings of the Technology Transfer Workshop, Held at ESA/ESTEC Noordwijk, The Netherlands, May 1994 (ESA SP-364, Aug. 1994).

Superelastic Fixation System Brochure, Memometal Inc., USA, Aug. 12, 2009.

Shape Memory Staple System for Arthrodesis and Skeletal Fixation of the Hand Brochure, Core Essence Orhtopaedics, Inc., 2009.

ENTact™ Septal Stapler, Product brochure by ENTrigue Surgical, Inc. (© 2009).

R. M. Sloan et al., "Orthopedic Fixation Devices," Radiographics at 823 (Sep. 1991).

J. Arthur, "Improving Operating Efficiency in Five Days," Lean Six Sigma for Hospitals, McGraw-Hill (2011).

K. Yamauchi et al. (ed.), "Shape Memory and Superelastic Alloys: Applications and Technologies" (2011).

BioResearch Innovations (BRI), "Memodyn Compression Staple," FDA 510(K) disclosure (01/04).

G. C. Taylor et al., "Complications of Internal Fixation," Podiatry Institute Educational Materials Update Chapter 79 (1992).

Wright Medical Technology, Inc., "Charlotte Compression Staple as described by Robert Anderson, MD; Bruce Cohen, MD; and W. Hodges Davis, MD" (2007).

A. A. Weinbroum et al., "Efficiency of the Operating Room Suite," American Journal of Surgery 244-250 (2003).

G. G. Porto, "Safety by Design: Ten Lessons From Human Factors Research," Journal of Healthcare Risk Management 43-50 (Fall 2011).

International Search Report for PCT/IB2018/05811, dated Jan. 28, 2019, PCT Application Counterpart to U.S. Appl. No. 15/844,133.

* cited by examiner

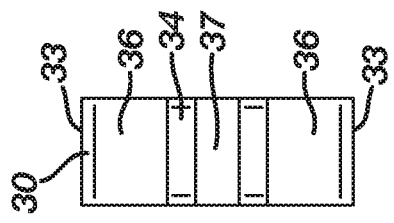
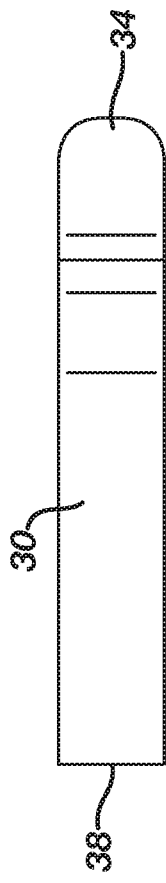
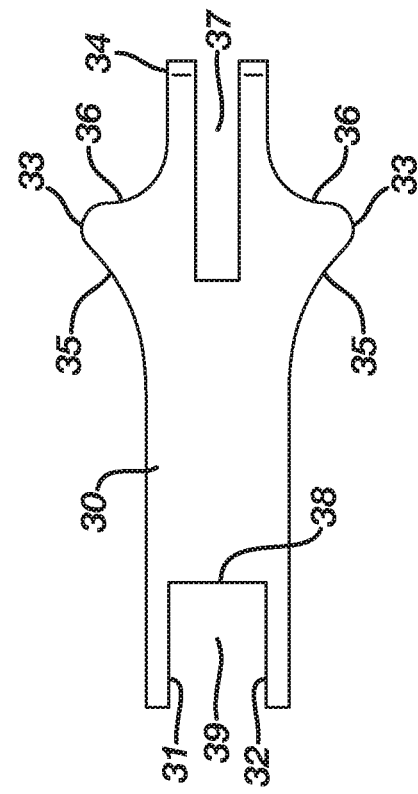
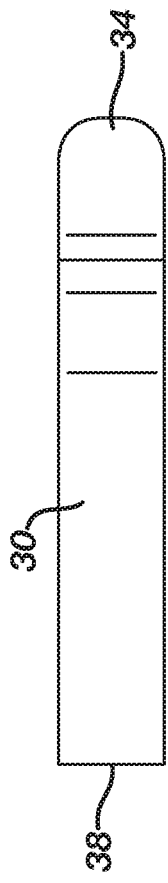
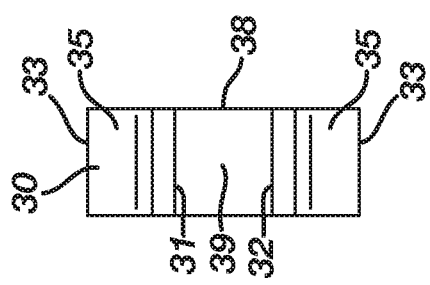

METHOD AND APPARATUS FOR LOADING AND IMPLANTING A SHAPE MEMORY IMPLANT

CROSS-REFERENCE TO RELATED APPLICATION

This present application claims all available benefit, under 35 U.S.C. § 119(e), of U.S. provisional patent application Ser. No. 62/574,845 filed Oct. 20, 2017. By this reference, the full disclosure of U.S. provisional patent application Ser. No. 62/574,845 is incorporated herein as though now set forth in its entirety.

BACKGROUND OF THE INVENTION

1. Field of the Invention

The present invention relates generally to an implantation device and, more particularly, but not way of limitation, to an implantation device designed for loading with a surgical implant and for subsequent delivery of the surgical implant. The implantation device uses jaws and a slider to secure a surgical implant and allow implantation into a patient.

2. Description of the Related Art

Shape memory implants are commonly used in surgical procedures that require the reattachment or fusing of tissue or bone. Shape memory implants can be composed of shape memory material such as Nitinol that allows the shape memory implants to have a first final shape and the ability to transform into a second shape. A shape memory implant can be either thermally activated, in which an external heating source or body temperature would be required to activate the implant, or mechanically activated, in which a constraining instrument would be required. A shape memory implant that requires mechanical constraint stores mechanical energy due to elastic (recoverable) deformation, and then releases the stored mechanical energy when the constraint is removed. In these types of implants, the implants are mechanically deformed into their second shape and maintained in their second shape by instrumentation such that, upon release from the instrumentation, the implants elastically deform from their second shape into their first final shape.

In surgical procedures, the elastic property of constrained shape memory implants is used as follows. Bones that require fixating are aligned, and the shape memory implant, which has been mechanically deformed to its second shape, is maintained in instrumentation and inserted between the bones. In the second shape, the legs of the implant are generally parallel. After insertion, the shape memory implant is released from the instrumentation, whereupon the shape memory implant elastically tries to return to its first final shape such that the shape memory implant maintains the bones fixated together. In the first final shape, the legs of the implant are converging at the tips. Because the shape memory implant stores mechanical energy, it continuously applies force to the fixated bones as the shape memory implant tries to transition from the second shape to the first final shape, which aids in the healing process.

Various types of instrumentation can be used for either maintaining the shape memory implants in their second shape or moving an implant from its first final shape to a temporary second shape. Some companies used metal forceps to open and insert the shape memory implant. These forceps have to be sterilized by a hospital, and then a shape memory implant can be placed on the forceps, opened to a desired position, and used for inserting the implant. Although potentially effective, forceps require the implant to be loaded into the forceps during surgery, which might be cumbersome and time consuming. In addition, forceps might be large which could hinder implantation of the shape memory implant into a patient during surgery. It is also possible that a physician using the forceps might damage the shape memory implant in various ways, such as stretching the implant beyond the second shape, fatiguing the implant, or causing metal-on-metal scraping of the implant with the instrument. Furthermore, forceps can be expensive instruments that require cleaning and sterilization after each surgery.

Other instrumentation includes plastic and disposable tools to maintain a shape memory implant in the second shape. This type of instrumentation can be preloaded and sterilized with the implant already in the second shape, and the implant can be pre-activated so that it does not require heating with an external heater or body temperature after use. One type of plastic and disposable instrument operates by having the implant fit inside a passage that is substantially the same diameter as the shape memory implant. By using this method, the instrumentation allows the shape memory implant to be preloaded prior to surgery. However, using instrumentation that substantially conforms to the profile of the shape memory implant can create several problems for a surgeon. First, this type of instrumentation often makes disengagement of the shape memory staple after implantation problematic. In particular, the shape memory implant sticks to the instrumentation due to the frictional engagement between the shape memory implant, which is trying to compress, and the passage of the instrumentation, resulting in a more difficult surgical procedure and the potential for a less than satisfactory fixation of tissue or bone. Second, this type of instrumentation results in an abrupt and sudden release of stored mechanical energy as the implant is removed from the device. This type of instrumentation accordingly provides no method of slowly transitioning the stored energy in the implant from the instrumentation to the bones being fixated. Finally, this type of instrumentation can result in entanglement during release, in which the implant legs begin to compress upon release and make extraction of this type of instrumentation more difficult.

Accordingly, an instrument that constrains a shape memory implant in its second shape, allows the shape memory implant to be preloaded and sterilized prior to surgery, simplifies removal of the shape memory implant after partial implantation, and controls the rate of release of tension would be beneficial.

SUMMARY OF THE INVENTION

In accordance with the present invention, an implant insertion device is designed for use with a shape memory implant movable between an unconstrained shape and an insertion shape. The shape memory implant includes a bridge interconnecting two or more legs and, more particularly, first, second, and third legs or first, second, third, and fourth legs. The implant insertion device maintains the shape memory implant in its insertion shape whereby the shape memory implant stores mechanical energy. Upon delivering the shape memory implant into tissue or bone using the implant insertion device, the implant insertion device releases the shape memory implant which attempts to move from its insertion shape to its unconstrained shape, thereby releasing mechanical energy into the tissue or bone.

The implant insertion device includes a body and a slider coupled with the body. The body includes first, second, third, and fourth arms terminating in a respective first, second, third, and fourth jaw that engages the shape memory implant. The first, second, third, and fourth arms include a splayed normally open position that spreads apart the first, second, third, and fourth jaws in a disengaged position. The first, second, third, and fourth arms further move from their splayed normally open position to a closed position that places the first, second, third, and fourth jaws in an engaged position. When the first, second, third, and fourth arms move from their splayed normally open position to their closed position, the first, second, third, and fourth arms travel along an arc toward a central axis of the body such that the first, second, third, and fourth jaws move angularly to their engaged position. The first, second, third, and fourth jaws in their disengaged position release the shape memory implant and in their engaged position maintain the shape memory implant in its insertion shape. The slider moves between an unclasped position that releases the first, second, third, and fourth jaws to return to their disengaged position and a clasped position that maintains the first, second, third, and fourth jaws in their engaged position. After delivery of the shape memory implant into tissue or bone and movement of the slider from its clasped position to its unclasped position, the first, second, third, and fourth arms return from their closed position to their splayed normally open position resulting in the first, second, third, and fourth jaws progressing from their engaged position to their disengaged position such that the implant insertion device releases the shape memory.

The first jaw resides in opposed relationship with the second jaw. The first and second jaws include alignment interfaces having complementary angled faces. Progression of the first and second jaws from their disengaged position to their engaged position moves the alignment interfaces of the first and second jaws into an abutting relationship. The alignment interfaces, due to their complementary angled faces, linearly displace the first and second jaws such that the first and second jaws engage the shape memory implant and maintain the shape memory implant in its insertion shape.

The third jaw resides in opposed relationship with the fourth jaw. The third and fourth jaws include alignment interfaces having complementary angled faces. Progression of the third and fourth jaws from their disengaged position to their engaged position moves the alignment interfaces of the third and fourth jaws into an abutting relationship. The alignment interfaces, due to their complementary angled faces, linearly displace the third and fourth jaws such that the third and fourth jaws engage the shape memory implant and maintain the shape memory implant in its insertion shape.

The alignment interfaces of the first and second jaws each include a leading edge and a trailing edge. When the first, second, third, and fourth arms reside in their splayed normally open position, the leading edge of the alignment interface for the first jaw substantially aligns with the trailing edge of the alignment interface for the second jaw such that the leading edge of the alignment interface for the first jaw is located in a plane offset relative to a plane of the leading edge for the alignment interface of the second jaw.

The alignment interfaces of the third and fourth jaws each include a leading edge and a trailing edge. When the first, second, third, and fourth arms reside in their splayed normally open position, the leading edge of the alignment interface for the third jaw substantially aligns with the trailing edge of the alignment interface for the fourth jaw such that the leading edge of the alignment interface for the third jaw is located in a plane offset relative to a plane of the leading edge for the alignment interface of the fourth jaw.

The first, second, third, and fourth jaws each define a bridge channel. When the first, second, third, and fourth jaws reside in their engaged position, each bridge channel receives therein a portion of the bridge for the shape memory implant.

The first, second, third, and fourth jaws each include a leg interface. When the first, second, third, and fourth jaws reside in their engaged position, the leg interfaces of the first and third jaws each engage the first leg of the shape memory implant, the leg interface of the second jaw engages the second leg of the shape memory implant, and the leg interface of the fourth jaw engages the third leg of the shape memory implant such that the first, second, third, and fourth jaws maintain the shape memory implant in its insertion shape. Alternatively, when the first, second, third, and fourth jaws reside in their engaged position, the leg interface of the first jaw engages the first leg of the shape memory implant, the leg interface of the second jaw engages the second leg of the shape memory implant, the leg interface of the third jaw engages the third leg of the shape memory implant, and the leg interface of the fourth jaw engages the fourth leg of the shape memory implant such that the first, second, third, and fourth jaws maintain the shape memory implant in its insertion shape.

The first, second, third, and fourth jaws each include a slider guide. When the first, second, third, and fourth jaws reside in their engaged position, the slider guides of the first and second jaws align and the slider guides of the third and fourth jaws align such that the slider in its clasped position resides over the slider guides thereby maintaining the first, second, third, and fourth jaws in their engaged position.

It is therefore an object of the present invention to provide an implant insertion device that maintains a shape memory implant in an insertion shape.

It is another object of the present invention to provide an implant insertion device that delivers the shape memory implant into tissue or bone.

It is a further object of the present invention to provide an implant insertion device that, upon releasing the shape memory implant, the shape memory attempts to move from an insertion shape to an unconstrained shape, thereby releasing mechanical energy into the tissue or bone.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

BRIEF DESCRIPTION OF DRAWINGS

FIG. 22 is a front view illustrating the slider of the implant insertion device according to the first embodiment.

FIG. 23 is a right side view illustrating the slider of the implant insertion device according to the first embodiment.

FIG. 24 is a left side view illustrating the slider of the implant insertion device according to the first embodiment.

FIG. 25 is a top view illustrating the slider of the implant insertion device according to the first embodiment.

FIG. 26 is a bottom view illustrating the slider of the implant insertion device according to the first embodiment.

DETAILED DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

Figure 1:
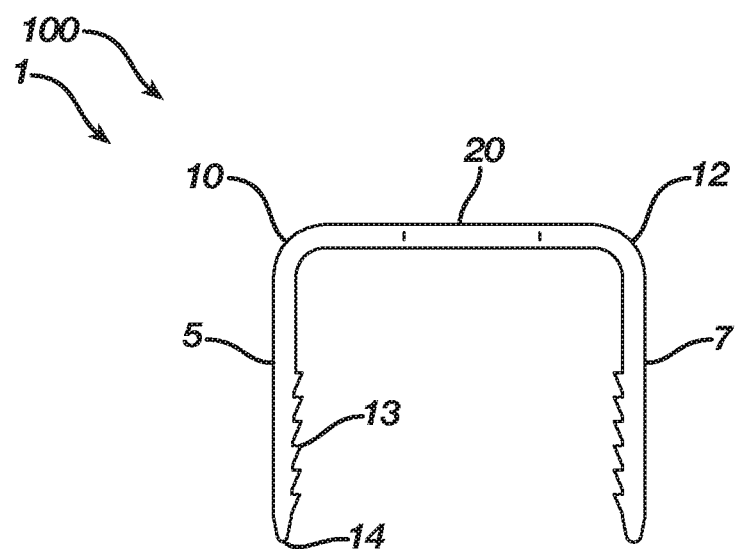
FIG. 1 is a side view illustrating a first implant in its insertion shape.
Figure 2:
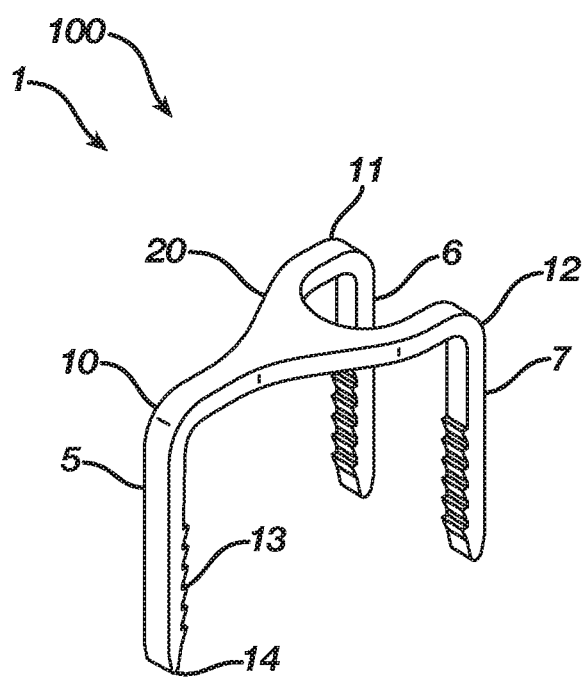
FIG. 2 is a perspective view illustrating the first implant in its insertion shape.

FIGS. 1 and 2 illustrate a first orthopedic implant 1 in an insertion shape 100. The implant 1 consists of three or more legs, such as the three legs 5, 6, and 7 shown in FIGS. 1 and 2. Although the three legs 5, 6, and 7 produce a triangular shape, any number of other shapes or multi-legged designs exist, such as that disclosed herein in with reference to FIGS. 27-30. Each leg 5, 6, and 7 is capable of penetrating into tissue or bone to anchor the implant 1. Barbs on each leg 5, 6, and 7, such as representative barb 13, provide resistance to movement when the implant 1 is inserted into tissue or bone. Any number of barbs can be on each leg 5, 6, and 7. A leg tip 14, which is on leg 5, but is representative of the leg tips on each leg, can be blunt or pointed for insertion into tissue or bone. A bridge 20 connects the three or more legs of the implant 1. Corners 10, 11, and 12 represent the location where the legs 5, 6, and 7 connect with the bridge 20. The corners 10, 11, and 12 can be of any radius such that the implant 1 conforms to tissue or bone when implanted. The bridge 20 as shown in FIG. 1 is mostly flat; however, there is any number of shapes for the bridge 20 that will connect with the legs 5, 6, and 7 and conform to tissue or bone after implantation.

The implant 1 is made of an elastic material suitable for orthopedic use, such as a shape memory material (e.g., Nitinol). In the insertion shape 100, the legs 5, 6, and 7 of implant 1 are substantially parallel to each other, such that the implant 1 easily inserts into holes drilled in tissue or bone. However, the insertion shape 100 is not the natural shape of the implant 1, and thus the legs 5, 6, and 7 must be constrained mechanically or the implant 1 must be chilled until it is in the martensitic state such the legs 5, 6, and 7 once deformed naturally remain in the insertion shape 100.

Figure 3:
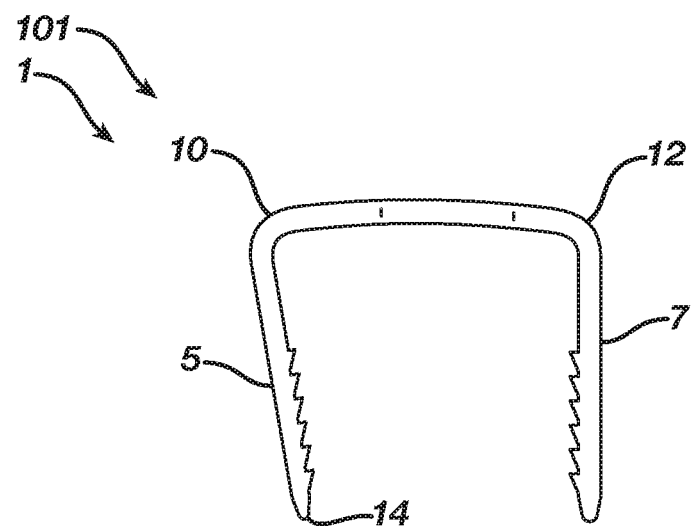
FIG. 3 is a side view illustrating the first implant in its unconstrained shape.
Figure 4:
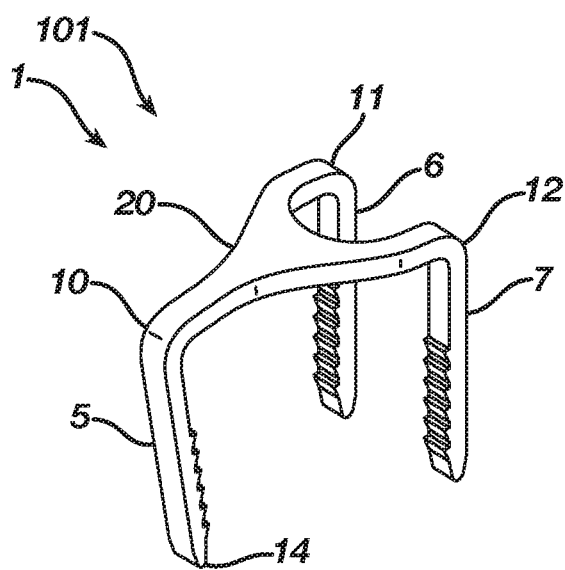
FIG. 4 is a perspective view illustrating the first implant in its unconstrained shape.

FIGS. 3 and 4 illustrate the first orthopedic implant 1 in an unconstrained shape 101. The implant 1 in its unconstrained shape 101 includes the leg 5 attempting to move inward due to the shape memory or superelastic property of the material near the corner 10. The leg 5 thus may no longer be parallel to the legs 6 and 7. This has occurred either because a mechanical constraint of the leg 5 has been removed, allowing it to swing inward, or because the leg 5 was previously chilled in a deformed martensite state and now has transitioned to its natural shape in the austenite phase. Furthermore, the bridge 20 may arch due to the same reasons, so as to bring the leg 5 closer to the legs 6 and 7. In these two ways, the implant 1 creates a compression force between the leg 5 and the legs 6 and 7. In addition to this motion, one of ordinary skill in the art could design the implant 1 to have any number of legs or any combination of movements. Although stationary in the first orthopedic implant 1, alternative embodiments of the legs 6 and 7 could move towards the leg 5 or towards each other.

Figure 5:
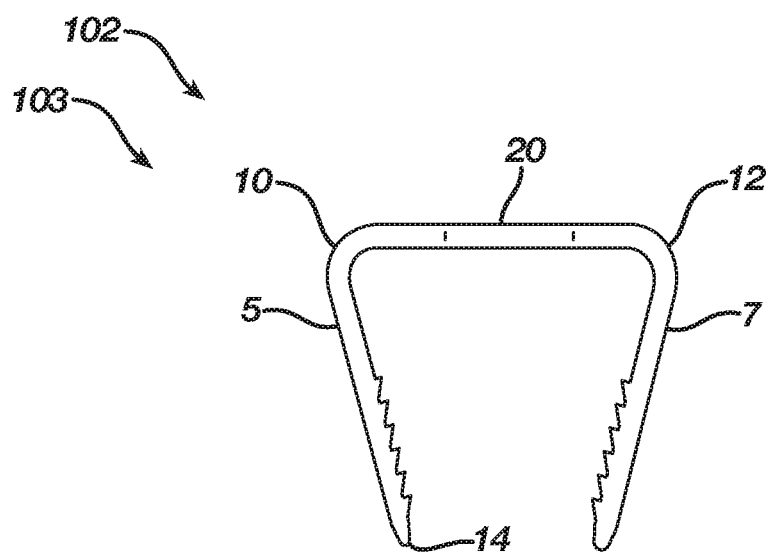
FIG. 5 is a side view illustrating a second implant in its unconstrained shape.
Figure 6:
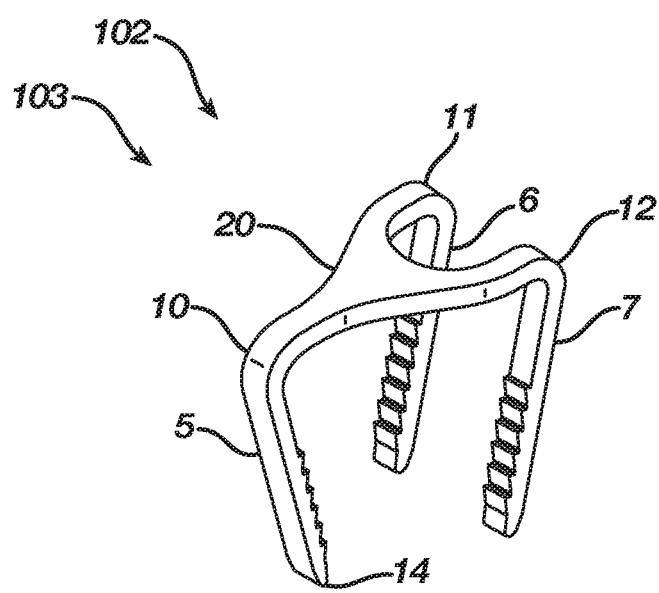
FIG. 6 is a perspective view illustrating the second implant in its unconstrained shape.

FIGS. 5 and 6 illustrate a second orthopedic implant 102 in an unconstrained shape 103. The second orthopedic implant 102 includes the same features as the first orthopedic implant 1, except that the legs 5, 6, and 7 all attempt to move under the action of shape memory or superelasticity to unconstrained non-parallel shapes. The material in the corners 10, 11, and 12 has now caused the legs 5, 6, and 7 to attempt to move from insertion substantially parallel shapes to compressed, non-parallel unconstrained shapes either due to release of a mechanical constraint on the legs 5, 6, and 7 or due to a phase change from chilled martensite to the austenite phase. In this way, additional compressive force is created by the legs 5, 6, and 7 of the implant 102.

Figure 7:
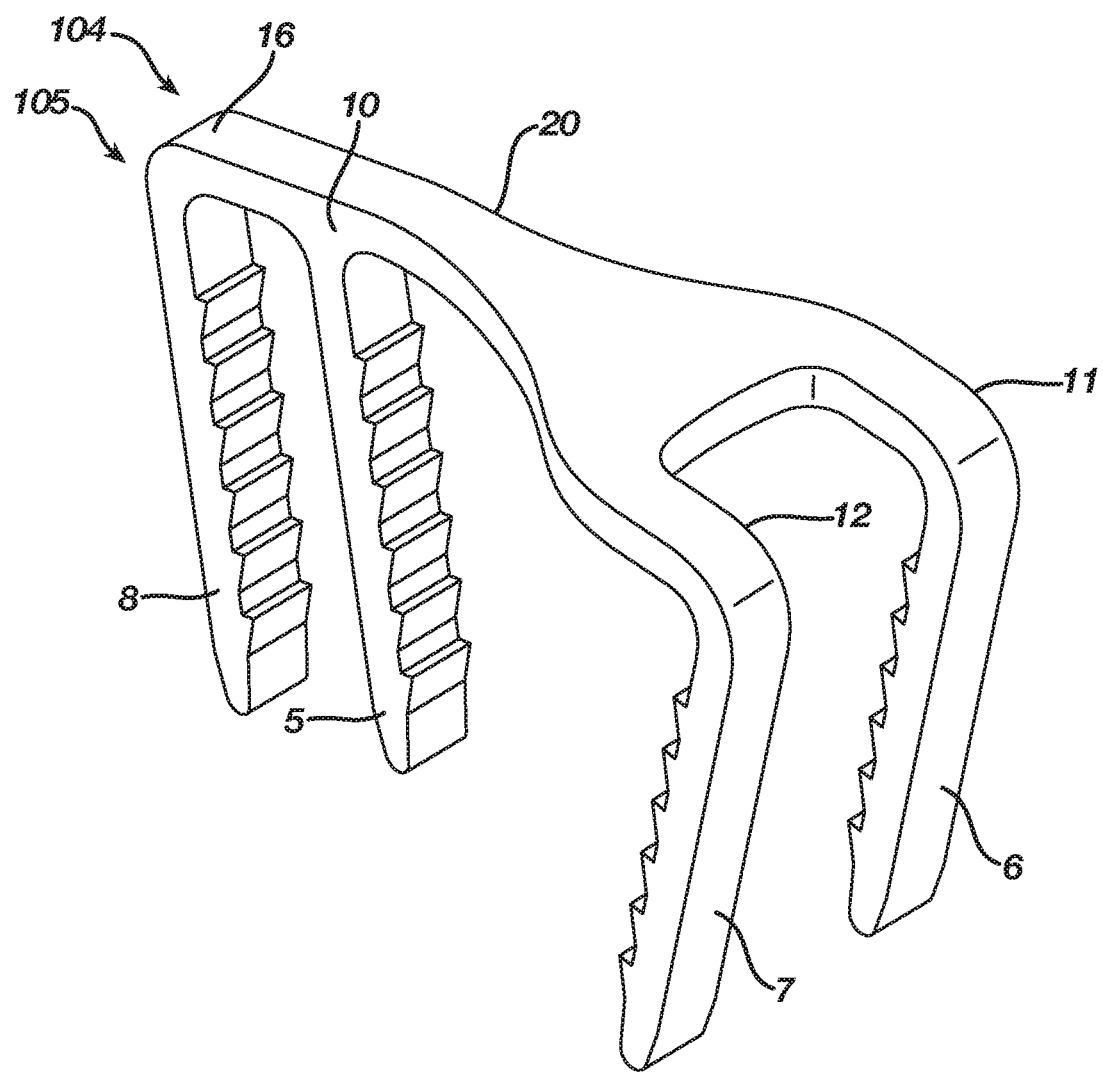
FIG. 7 is a perspective view illustrating the third implant in its unconstrained shape.

FIG. 7 illustrates a third orthopedic implant 104 in an unconstrained shape 105. The third orthopedic implant 104 incorporates features of either the first orthopedic implant 1 or the second orthopedic implant 102. In particular, the legs 6 and 7 of the third orthopedic implant 104 attempt to move under the action of shape memory or superelasticity between unconstrained non-parallel shapes and insertion substantially parallel shapes. The leg 5 may remain in an insertion substantially parallel shape or alternatively may move under the action of shape memory or superelasticity between an unconstrained non-parallel shape and insertion substantially parallel shape. The third orthopedic implant 104 in addition to the leg 5 includes a leg 8 connected with the bridge 20 at a corner 16 and in-line with the leg 5 to increase the pull-out strength of the third orthopedic implant 104. The leg 8 may remain in an insertion substantially parallel shape or alternatively may attempt to move with the leg 5 between an unconstrained non-parallel shape and insertion substantially parallel shape.

FIGS. 8-20 illustrate an implant insertion device 50 according to a first embodiment. The implant insertion device 50 as shown in FIGS. 8-20 engages a third orthopedic implant 104 and constrains the third orthopedic implant 104 in its insertion shape 106 such that a surgeon may insert the third orthopedic implant 104 into tissue or bone during surgery. Although the implant insertion device 50 will be described in combination with the third orthopedic implant 104, one of ordinary skill in the art will recognize that the implant insertion device 50 engages either a first orthopedic implant 100 or a second orthopedic implant 102 and constrains the first orthopedic implant 100 or the second orthopedic implant 102 in their insertion shape such that a surgeon may insert the first orthopedic implant 100 or the second orthopedic implant 102 into tissue or bone during surgery.

The implant insertion device 50 includes a body 51 and a slider 30 that moves between an unclasped position and a clasped position. The implant insertion device 50 resides in either an implant disengagement position 41 (shown in FIGS. 8, 10, and 12) or an implant engagement position 42 (shown in FIGS. 9, 11, and 13) and is movable therebetween. In the implant disengagement position 41, the third orthopedic implant 104 slips in or out of the implant insertion device 50 with no obstruction. In the implant engagement position 42, the implant insertion device 50 engages the third orthopedic implant 104 and maintains the third orthopedic implant 104 constrained in its insertion shape 106. In addition, the implant insertion device 50 allows a surgeon to manipulate the third orthopedic implant 104 and insert the third orthopedic implant 104 into tissue or bones requiring fixating.

The body 51 of the implant insertion device 50 includes a slider receiver 53, a first side 54, a second side 55, a handle 56 having a top 57, arms 58 and 59, and arms 60 and 61. A flat groove in both the first side 54 and the second side 55 of the body 51 defines the slider receiver 53 such that the slider receiver 53 receives a portion of the slider 30 to allow the securing of the slider 30 over the slider receiver 53 and thus to the body 51. The handle 56 provides a gripping surface on the first side 54 and the second side 55 of the body 51. The gripping surface of the handle 56 allows a surgeon to manipulate the implant insertion device 50 and therefore the third orthopedic implant 104 that is secured thereto. The arms 58 and 59 of the body 51 extend from the body 51 at the first side 54 and include a jaw 70 and a jaw 71, respectively. The arms 60 and 61 of the body 51 extend from the body 51 at the second side 55 and include a jaw 72 and a jaw 73, respectively. The arms 58-61 reside in a normally open position (shown in FIGS. 8, 10, and 12) whereby the arms 58-61 are spread apart and are movable to a closed position (shown in FIGS. 9, 11, and 13) whereby the arms 58-61 are adjacent. Movement of the arms 58-61 from their normally open position to their closed position progresses the jaws 70-73 from a disengaged position to an engaged position. The implant insertion device 50 may be manufactured from any suitable resilient material; however, in the first embodiment the implant insertion device 50 is made from plastic.

In the first embodiment, the body 51 of the implant insertion device 50 is manufactured in one piece using a mold. However, the body 51 of the implant insertion device 50 could be manufactured in two separate pieces. In particular, the arms 58 and 59, the jaws 70 and 71, and a portion of the handle 56 may form a first piece. The arms 60 and 61, the jaws 72 and 73, and a portion of the handle 56 may form a second piece. The two separate pieces are then fastened together using any suitable means such as a hinge or an adhesive to create the body 51.

The jaws 70-73 each include a slider guide 74-77, respectively, that interacts with the slider 30 as the slider 30 moves between its unclasped position to its clasped position. The jaws 70-73 each include a bridge interface 78-81, respectively, defining a bridge channel 86-89, respectively, that receives a portion of the bridge 20 therein. The jaws 70-73 each include a leg interface 82-85, respectively, that engages a portion of a leg 5, 6, or 7, respectively, below the bridge 20. The jaws 70-73 each include an alignment interface 90-93, respectively, that interacts with an opposing alignment interface 90-93 during movement of the jaws 70-73 from their disengaged position (shown in FIGS. 8, 10, and 12) to their engaged position (shown in FIGS. 9, 11, and 13). The alignment interfaces 90 and 92 each include a leading edge 94 and a trailing edge 95 located in a plane offset relative to a plane of the leading edge 94 such that the alignment interfaces 90 and 91 angle across their faces from the leading edge 94 to the trailing edge 95. The alignment interfaces 91 and 93 each include a leading edge 96 and a trailing edge 97 located in a plane offset relative to a plane of the leading edge 96 such that the alignment interfaces 91 and 93 angle across their faces from the leading edge 97 to the trailing edge 97. In locating the trailing edges 95 of the alignment interfaces 90 and 92 offset relative to their leading edges 94 and the trailing edges 97 of the alignment interfaces 91 and 93 offset relative to their leading edges 96, the angles across the faces of the alignment interfaces 90 and 92 are complementary relative to the angles across the faces of the alignment interfaces 91 and 93.

The jaws 70-73 travel between their disengaged position and their engaged position to facilitate the securing of the third orthopedic implant 104 in the implant insertion device 50 as well as the removal of the third orthopedic implant 104 from the implant insertion device 50. As the implant insertion device 50, via manipulation of the arms 58-61 from their normally open position to their closed position, moves from its implant disengagement position 41 to its implant engagement position 42, the jaws 70-73 move angularly and linearly when progressing from their disengaged position to their engaged position. In particular, the jaws 70 and 71 move into abutting relationship at their alignment interfaces 90 and 91, and the jaws 72 and 73 move into abutting relationship at their alignment interfaces 92 and 93. In addition, the slider guide 75 moves into abutting relationship over the slider guide 74 and the slider guide 77 moves into abutting relationship over the slider guide 76 such that the slider guides 74-77 interact with the slider 30. The jaws 70-73 are complementary in shape and interact to form a unitary device in their engaged position that grasps the third orthopedic implant 104. The movement of the jaws 70-73 in engaging the third orthopedic implant 104 and constraining the third orthopedic implant 104 in its insertion shape 106 will be described more fully herein.

Figure 8:
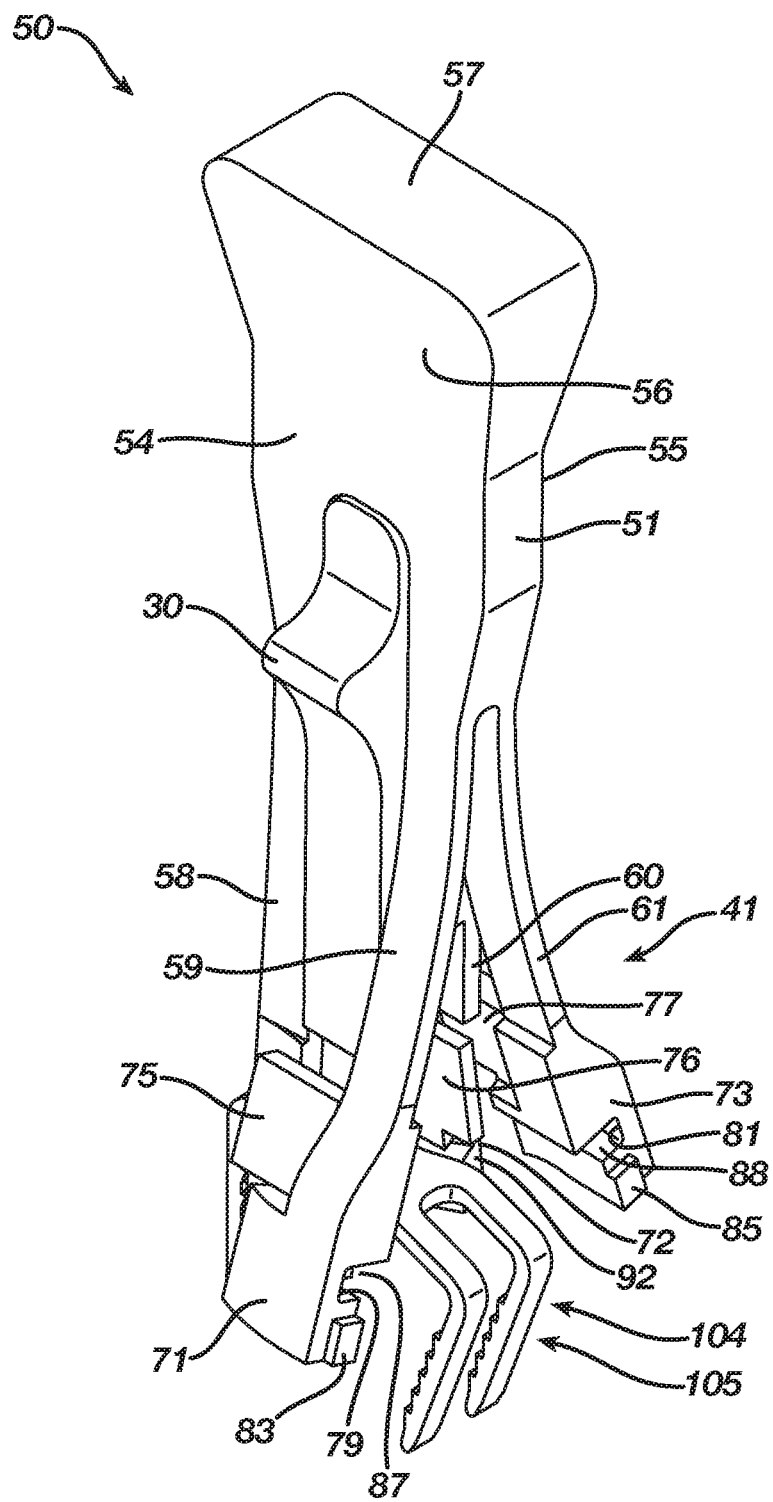
FIG. 8 is a perspective view illustrating a third implant and an implant insertion device according to a first embodiment in an implant disengagement position.
Figure 9:
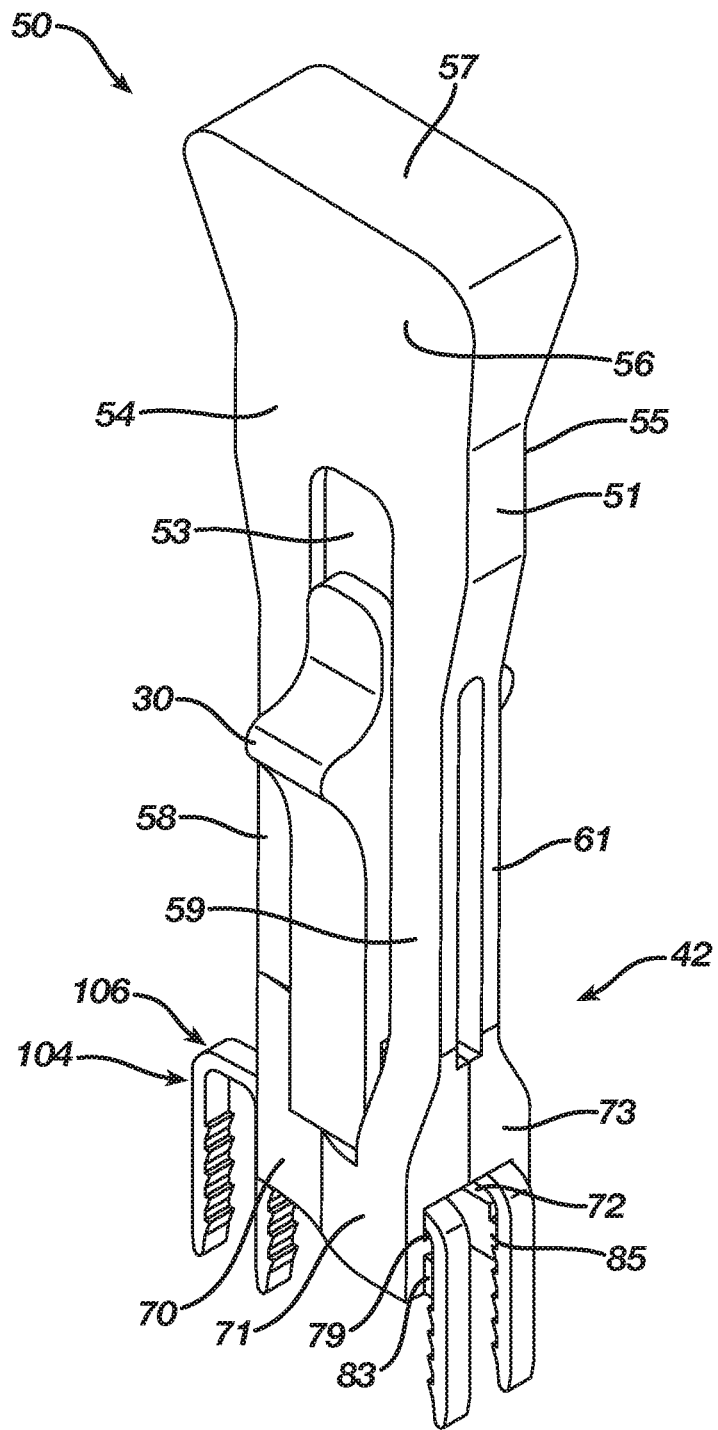
FIG. 9 is a perspective view illustrating the third implant and the implant insertion device according to the first embodiment in an implant engagement position.

FIGS. 21-26 illustrate the slider 30. The slider 30 includes a clasp 38 having a clasping surface 31 and a clasping surface 32 that define a slot 39 therebetween. The slider 30 defines a slot 37 at a slider tail 34. The slider 30 further includes an actuator 33 having front faces 35 and back faces 36. The slot 37 allows the slider 30 to engage the body 51 and move between its unclasped and clasped positions. In particular, placement of the slider 30 within the body 51 by inserting the slider 30 between the arms 58-61 such that the slider 30 engages with the slider receiver 53 of the body 51 via the slot 37 secures the slider 30 with the body 51. The actuator 33 allows a user to operate the slider 30 by moving the slider 30 between its unclasped and its clasped position. Specifically, as shown in FIGS. 8 and 9, when a user pushes against the back faces 36 of the actuator 33, the slider 30 moves within the arms 58-61 and along the slider receiver 53 from its unclasped position to its clasped position. Conversely, when a user pulls against the front faces 35 of the actuator 33, the slider 30 moves within the arms 58-61 and along the slider receiver 53 from its clasped position to its unclasped position.

The clasp 38 of the slider 30 allows the slider 30 to hold the jaws 70-73 in their engaged position. Particularly, when the slider 30 moves from its unclasped position to its clasped position, the clasp 38 grasps the slider guides 74-77 in that the slider guides 74-77 enter the clasp 38 via its slot 39. More particularly, the clasping surface 31 frictionally engages the slider guide 75, which resides over the slider guide 74, and the clasping surface 32 frictionally engages the slider guide 77, which resides over the slider guide 76. The frictional engagement between the clasping surfaces 31 and 32 and slider guides 74-77, respectively, holds the jaws 70-73 in their engaged position.

Figure 10:
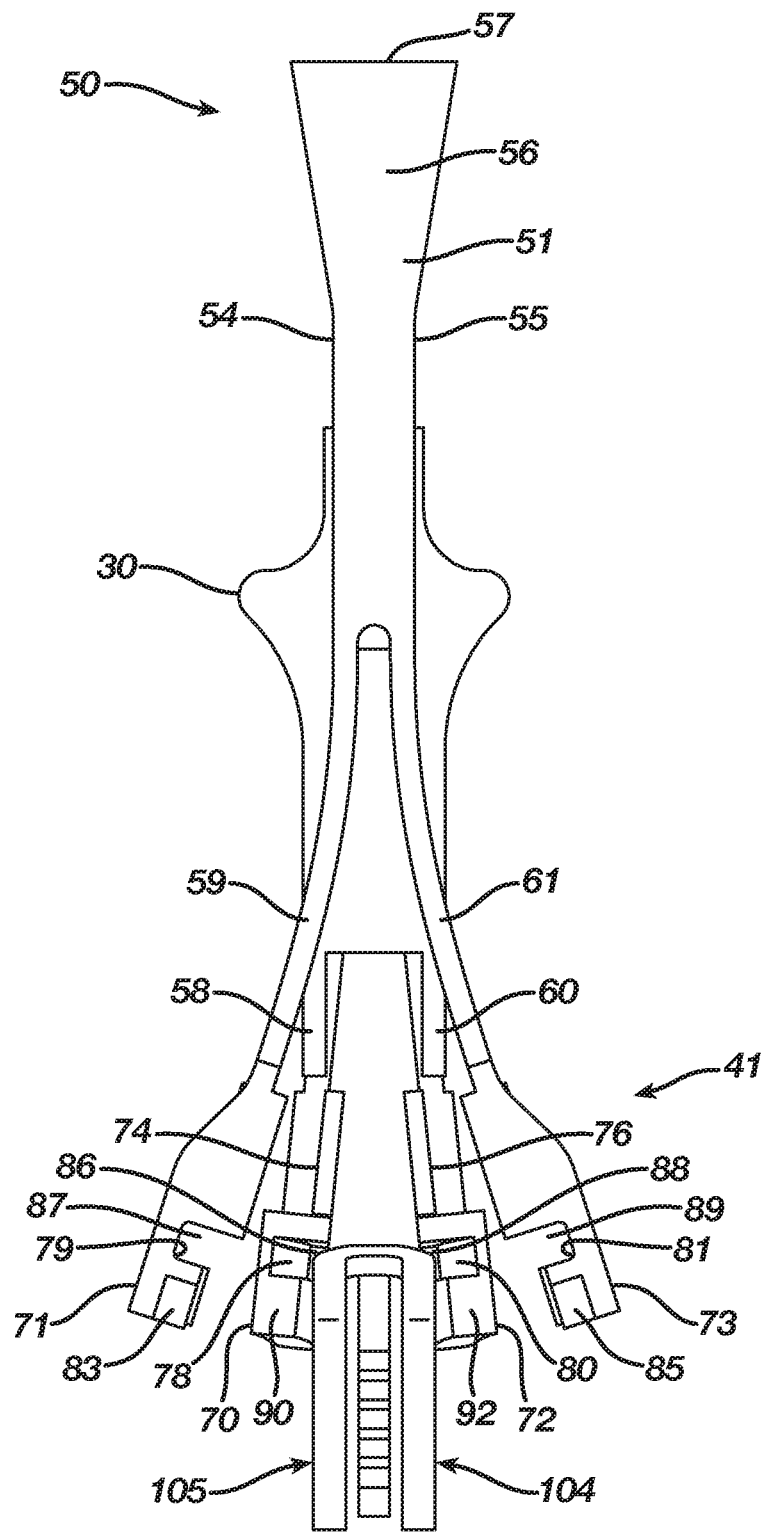
FIG. 10 is a front view illustrating the third implant and the implant insertion device according to the first embodiment in its implant disengagement position.
Figure 12:
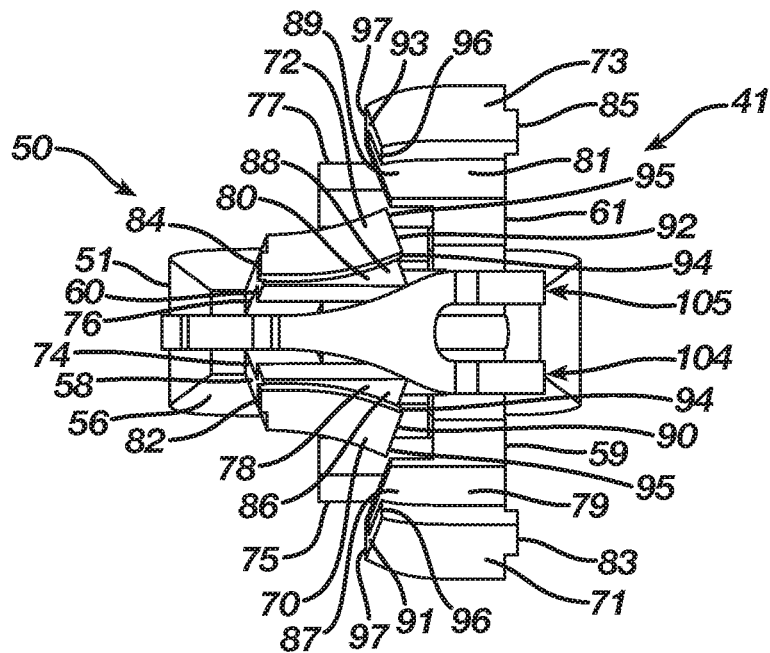
FIG. 12 is a bottom view illustrating the third implant and the implant insertion device according to the first embodiment in its implant disengagement position.
Figure 13:
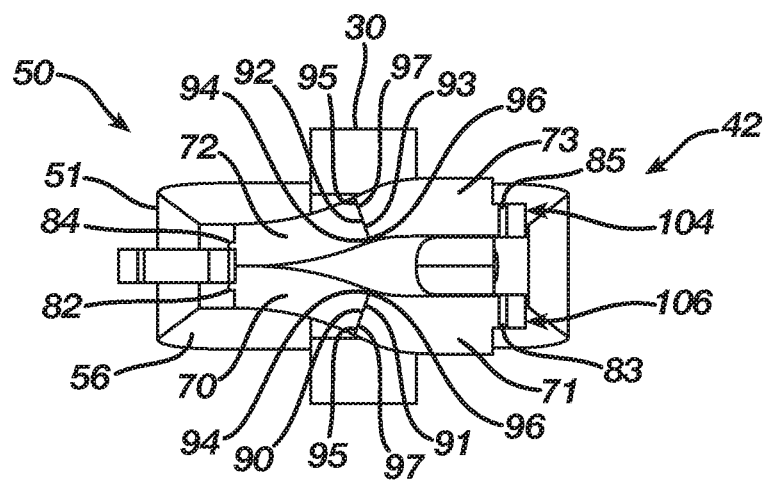
FIG. 13 is a bottom view illustrating the third implant and the implant insertion device according to the first embodiment in its implant engagement position.
Figure 14:
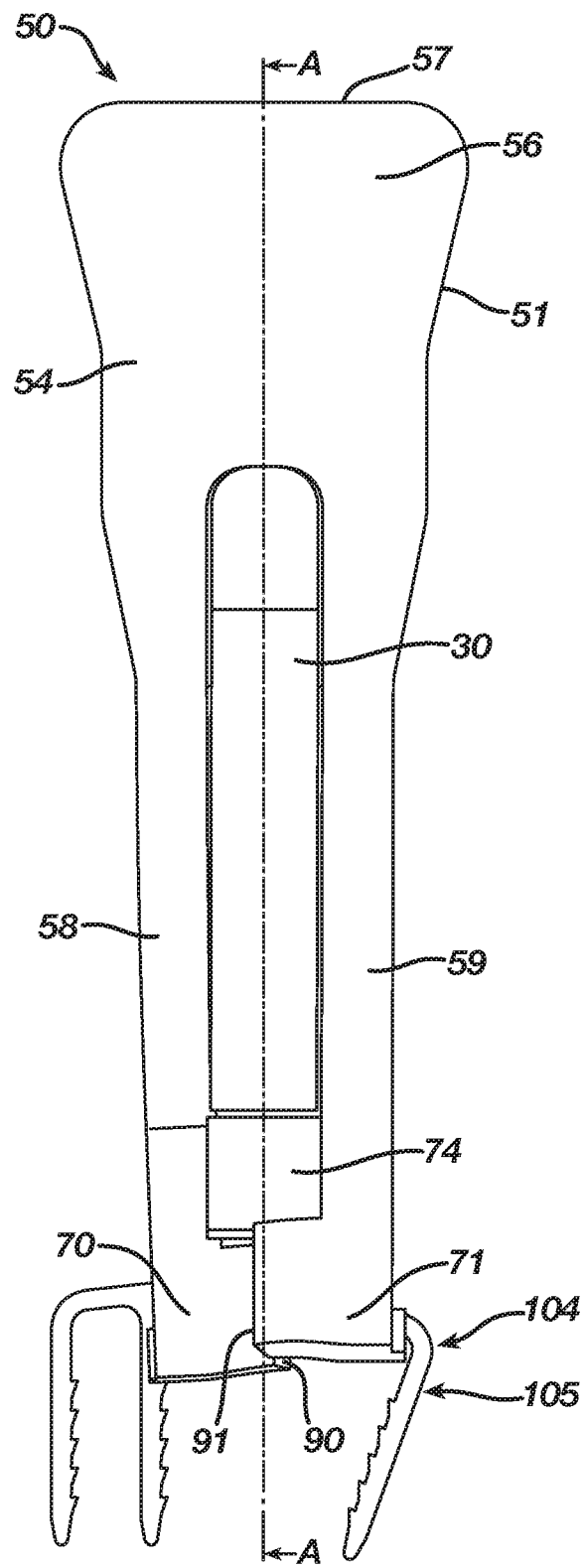
FIG. 14 is a side view illustrating the third implant and the implant insertion device according to the first embodiment in its implant disengagement position.
Figure 15:
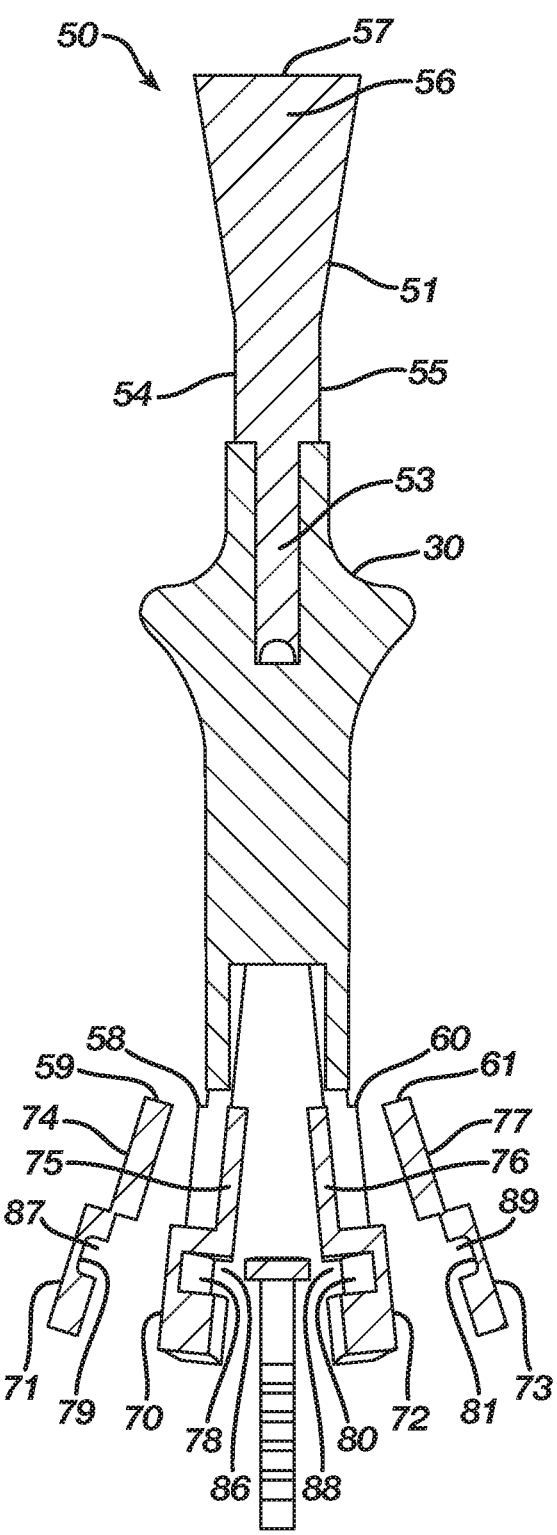
FIG. 15 is a cross-sectional view taken along lines A-A of FIG. 15 illustrating the third implant and the implant insertion device according to the first embodiment in its implant disengagement position.
Figure 16:
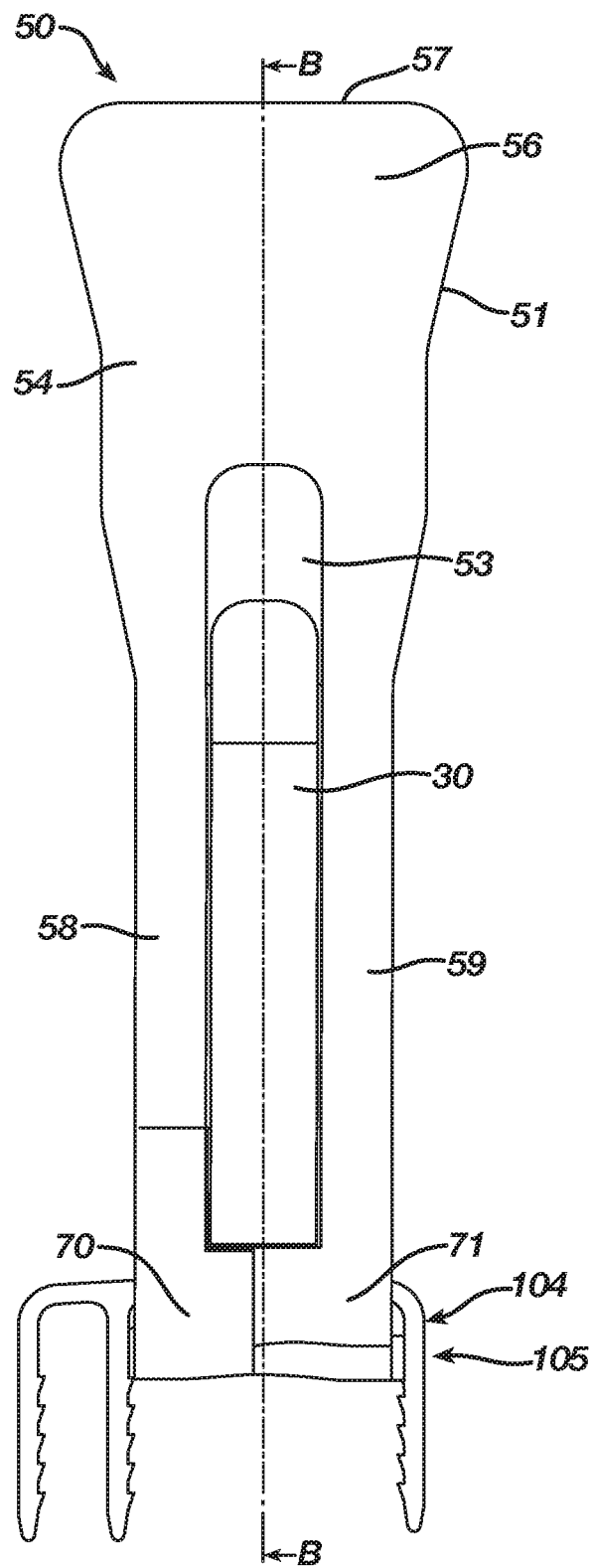
FIG. 16 is a side view illustrating the third implant and the implant insertion device according to the first embodiment in its implant engagement position.

The implant insertion device 50 according to the first embodiment prior to its loading with a third orthopedic implant 104 begins in its implant disengagement position 41 illustrated in FIGS. 8, 10, and 12. In the implant disengagement position 41, the slider 30 resides in its unclasped position whereby the slider 30 is disengaged from the slider guides 74-77 such that the arms 58-61 are splayed in their normally open position and the jaws 70-73 are spread apart in their disengaged position. Referring specifically to FIGS. 8, 10, and 15, the arms 58-61 due to their construction from a resilient material reside at a first end angle relative to a central axis of the implant insertion device 50 when viewed at an end thereof. Furthermore, referring specifically to FIG. 14, the arms 58-61 due to their construction from a resilient material reside at a first side angle relative to a central axis of the implant insertion device 50 when viewed at a side thereof. Moreover, when the arms 58-61 reside at their first side angle, the leading edges 96 of the alignment interfaces 91 and 93, respectively, substantially align with the trailing edges 95 of the alignment interfaces 90 and 92 such that the leading edges 96 of the alignment interfaces 91 and 93 are located in a plane offset relative to a plane of the leading edges 94 for the alignment interfaces 90 and 92.

When loading the implant insertion device 50, a third orthopedic implant 104 in its unconstrained shape 105 is located between the jaws 70-73 with its bridge 20 aligned with the bridge channels 86-89 of the jaws 70-73. The implant insertion device 50 progresses from its implant disengagement position 41 to its engagement position 42 such that the arms 58-61 move to their closed position and the jaws 70-73 contact the third orthopedic implant 104 and manipulate the third orthopedic implant 104 to its insertion shape 106 as the jaws 70-73 travel from their disengaged position to their engaged position. The slider 30 moves from its unclasped position to its clasped position whereby the slider 30 engages the slider guides 74-77 to hold the arms 58-61 in their closed position and the jaws 70-73 in their engaged position that constrains the third orthopedic implant 104 in its insertion shape 106.

Alternatively, a third orthopedic implant 104 manipulated to its insertion shape 106 and held therein is located between the jaws 70-73 with its bridge 20 aligned with the bridge channels 86-89 of the jaws 70-73. The implant insertion device 50 progresses from its implant disengagement position 41 to its engagement position 42 such that the arms 58-61 move to their closed position and the jaws 70-73 contact the third orthopedic implant 104 as the jaws 70-73 travel from their disengaged position to their engaged position. The slider 30 moves from its unclasped position to its clasped position whereby the slider 30 engages the slider guides 74-77 to hold the arms 58-61 in their closed position and the jaws 70-73 in their engaged position that constrains the third orthopedic implant 104 in its insertion shape 106.

Figure 11:
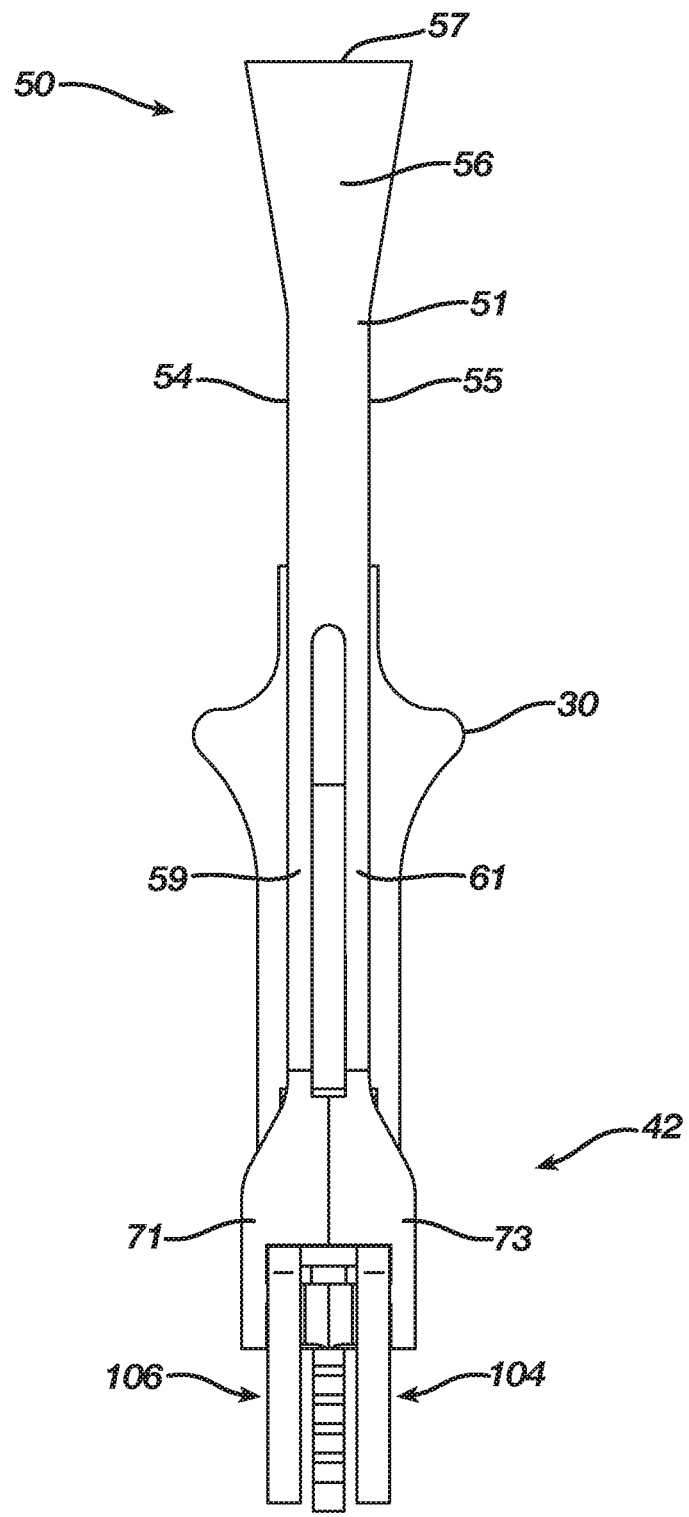
FIG. 11 is a front view illustrating the third implant and the implant insertion device according to the first embodiment in its implant engagement position.
Figure 17:
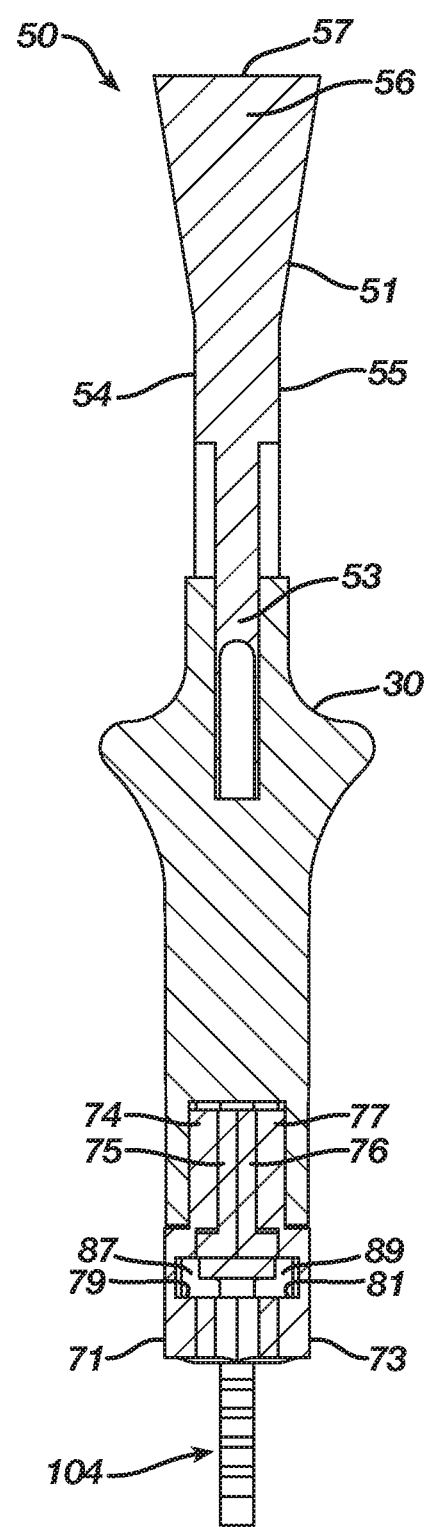
FIG. 17 is a cross-sectional view taken along lines B-B of FIG. 16 illustrating the third implant and the implant insertion device according to the first embodiment in its implant engagement position.
Figure 18:
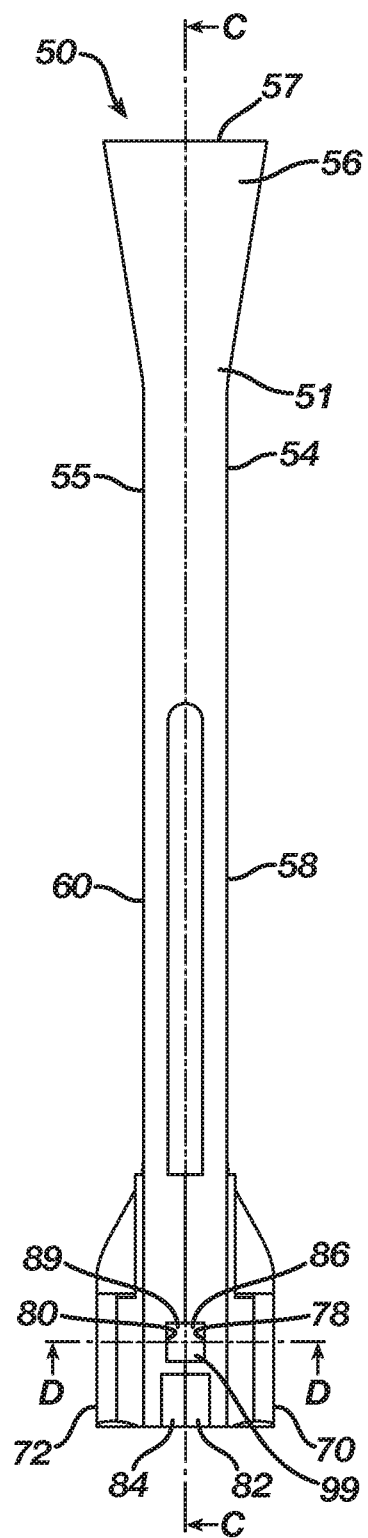
FIG. 18 is a rear view illustrating the implant insertion device according to the first embodiment in its implant engagement position.
Figure 19:
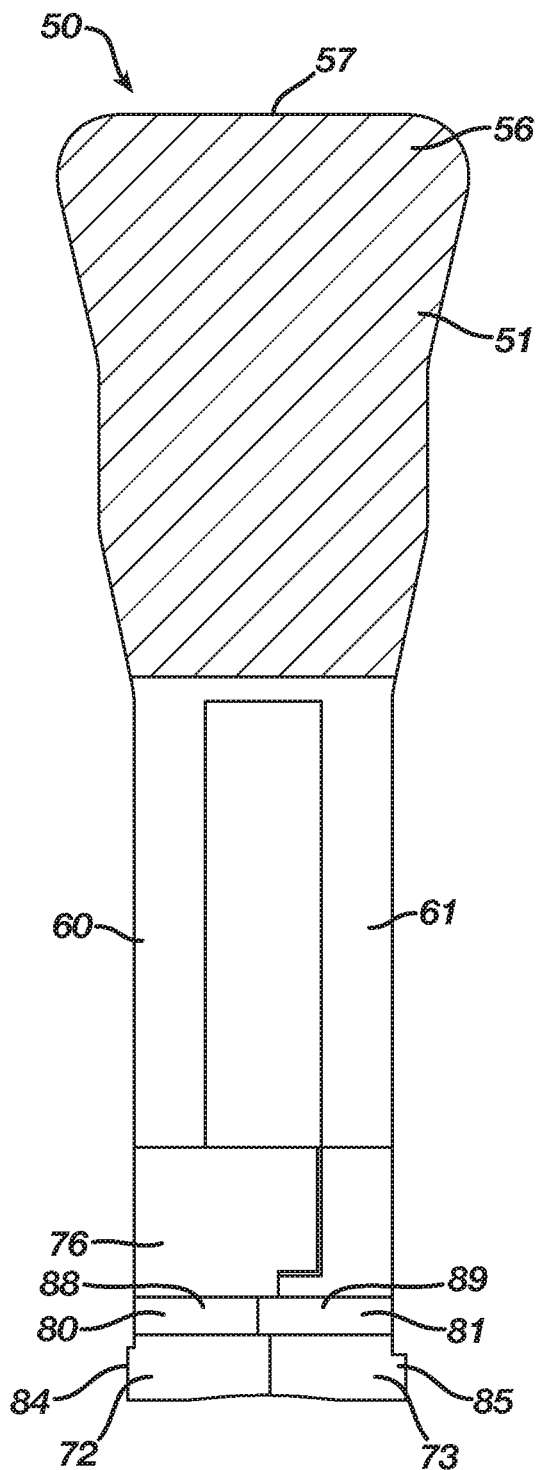
FIG. 19 is a cross-sectional view taken along lines C-C of FIG. 18 illustrating the implant insertion device according to the first embodiment in its implant engagement position.
Figure 20:
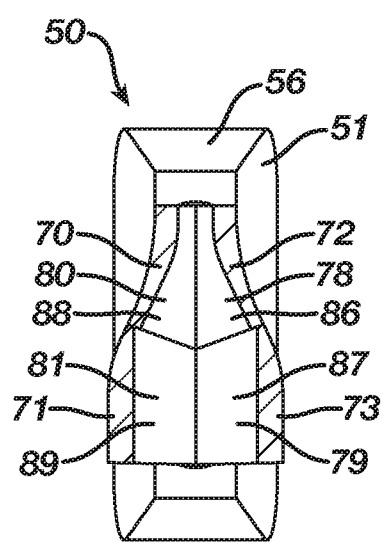
FIG. 20 is a cross-sectional view taken along lines D-D of FIG. 18 illustrating the implant insertion device according to the first embodiment in its implant engagement position.
Figure 21:
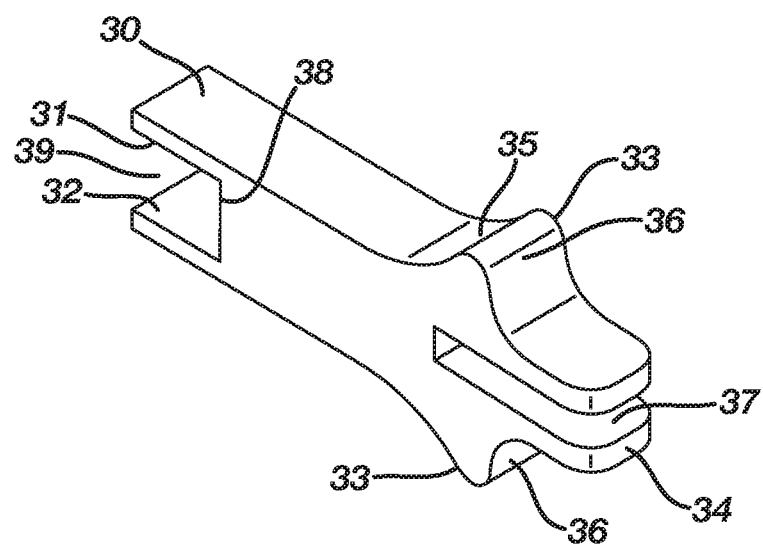
FIG. 21 is a perspective view illustrating a slider of the implant insertion device according to the first embodiment.

Referring specifically to FIGS. 9, 11, and 17, the arms 58-61 due to their construction from a resilient material move along an arc toward the central axis of the implant insertion device 50 when viewed at an end thereof from the first end angle to a second end angle which is less than the first end angle. In the first embodiment, the first end angle is any angle greater than 0° relative to the central axis of the implant insertion device 50 when viewed at an end thereof that allows insertion of a third orthopedic implant 104 in its unconstrained shape 105 between the jaws 70-73, and the second end angle is substantially equal to 0° relative to a central axis of the implant insertion device 50 when viewed at an end thereof. Furthermore, referring specifically to FIG. 16, the arms 58-61 due to their construction from a resilient material move along an arc away from the central axis of the implant insertion device 50 when viewed at a side thereof from the first side angle to a second side angle which is less than the first side angle. In the first embodiment, the first side angle is any angle greater than 0° relative to the central axis of the implant insertion device 50 when viewed at a side thereof that allows insertion of a third orthopedic implant 104 in its unconstrained shape 105 between the jaws 70-73, and the second end angle is substantially equal to 0° relative to the central axis of the implant insertion device 50 when viewed at a side thereof.

When loading the implant insertion device 50 with a third orthopedic implant 104 in its unconstrained shape 105, movement of the arms 58-61 from their normally open position to their closed position and the jaws 70-73 from their disengaged position to their engaged position contacts the bridge interface 81 with a portion of the bridge 20 adjacent the corner 11 and inserts the portion into the bridge channel 89. Likewise, the bridge interface 79 contacts a portion of the bridge 20 adjacent the corner 12 and inserts the portion into the bridge channel 87. Similarly, the bridge interfaces 78 and 80 contact a portion of the bridge 20 adjacent the corner 10 such that the portion inserts between the bridge channels 86 and 88 and extends through an opening 99 defined by the bridge channels 86 and 88. In addition, the leg interface 85 contacts a portion of the leg 6 below the corner 11, and the leg interface 83 contacts a portion of the leg 7 below the corner 12. Moreover, the leg interfaces 82 and 84 contact a portion of the leg 5 below the corner 10. When moved to their closed position, the arms 58-61 travel along an arc toward the central axis of the implant insertion device 50 when viewed at an end thereof from the first end angle shown in FIG. 10 to the second end angle shown in FIG. 11.

Progression of the jaws 70-73 from their disengaged position to their engaged position begins with the leading edges 96 of the alignment interfaces 91 and 93 contacting the trailing edges 95 of the alignment interfaces 90 and 92 and ends when the leading edges 96 and trailing edges 97 of the alignment interfaces 91 and 93 respectively reside adjacent the leading edges 94 and trailing edges 95 of the alignment interfaces 90 and 92 such that the alignment interfaces 91 and 93 abut their respective alignment interfaces 90 and 91. The offset of the trailing edges 95 and 97 respectively relative to the leading edges 94 and 96 and the resulting complementary angled faces of the alignment interfaces 90-91 and 92-93 facilitate movement of the arms 58-61 from their normally open position to their closed position as the alignment interfaces 91 and 93 travel into an abutting relationship with the alignment interfaces 90 and 92 because the complementary angled faces of the alignment interfaces 90-91 displace the jaw 70 linearly relative to the jaw 71 and the complementary angled faces of the alignment interfaces 92-93 displace the jaw 72 linearly relative to the jaw 73. Specifically, the jaws 70 and 71 and the jaws 72 and 73 move in opposing linear directions such that the jaw 71 engages the leg 6 at its leg interface 83, the jaw 73 engages the leg 7 at its the leg interface 85, and the jaws 70 and 71 engage the leg 5 at their leg interfaces 82 and 84. The opposing linear motion of the jaw 70 relative to the jaw 71 and the jaw 72 relative to the jaw 73 produces movement of the arms 58-61 along an arc away from the central axis of the implant insertion device 50 when viewed at a side thereof from their first side angle shown in FIG. 14 to their second side angle shown in FIG. 16. Moreover, the opposing linear motion of the jaw 70 relative to the jaw 71 and the jaw 72 relative to the jaw 73 progresses a third orthopedic implant 104 from its unconstrained shape 105 to its insertion shape 106 and further constrains the third orthopedic implant 104 in its insertion shape 106. Alternatively, when a third orthopedic implant 104 was previously manipulated to its insertion shape 106 and held therein, the opposing linear motion of the jaw 70 relative to the jaw 71 and the jaw 72 relative to the jaw 73 constrains the third orthopedic implant 104 in its insertion shape 106.

Movement of the arms 58-61 from their normally open position to their closed position and the jaws 70-73 from their disengaged position to their engaged position further progresses the slider guide 75 into abutting relationship over the slider guides 74 and the slider guide 77 into abutting relationship over the slider guide 76. Once the slider guides 75 and 77 reside in abutting relationship over their respective slider guides 74 and 76, the slider 30 moves within the arms 58-61 and along the slider receiver 53 from its unclasped position to its clasped position. In particular, the clasp 38 of the slider 30 slides over the slider guides 74-77 such that the clasping surface 31 frictionally engages the slider guide 75, which resides over the slider guide 74, and the clasping surface 32 frictionally engages the slider guide 77, which resides over the slider guide 76. The frictional engagement between the clasping surfaces 31 and 32 and slider guides 74-77, respectively, holds the jaws 70-73 in their engaged position. The jaws 70-73 in their engaged position are unitary in that portions of the bridge 20 reside in the bridge channels 86-89 while the leg interfaces 83 and 85 abut a respective portion of the leg 6 and 7 and the leg interfaces 82 and 84 abut a portion of the leg 5 whereby the closed jaws 70-73 and thus the implant insertion device 50 constrain a third orthopedic implant 104 in its insertion shape 106.

In a first method to receive a third orthopedic implant 104, the implant insertion device 50 begins in its implant disengagement position 41 wherein the arms 58-61 reside in their normally open position and the jaws 70-73 reside in their disengaged position. The third orthopedic implant 104 is mechanically deformed from its unconstrained shape 105 into its insertion shape 106 such that the third orthopedic implant 104 stores mechanical energy. After being mechanically deformed from s unconstrained shape 105 to its insertion shape 106, the third orthopedic implant 104 is placed between the jaws 70-73 with its bridge 20 aligned with the bridge channel 86-89 of the jaws 70-73.

Once the third orthopedic implant 104 is placed between the jaws 70-73, the arms 58-61 and the jaws 70-73 are moved respectively from their normally open position to their closed position and from their disengaged position to their engaged position. In progressing from their disengaged position to their engaged position, the jaws 70-73 move angularly along an arc toward the central axis of the implant insertion device 50 when viewed at an end thereof and, due to their angled alignment interfaces 90-93, linearly away from the central axis of the implant insertion device 50 when viewed at a side thereof. The movement of the jaws 70-73 from their disengaged position to their engaged position places portions of the bridge 20 in the bridge channels 86-89 and abuts the leg interfaces 83 and 85 with a respective portion of the leg 6 and 7 and the leg interfaces 82 and 84 with a portion of the leg 5. Progressing the slider 30 from its unclasped position to its clasped position frictionally engages its clasp 38 with the slider guides 74-77 thereby closing the jaws 70-73 in their engaged position. Securing the third orthopedic implant 104 between the jaws 70-73 maintains the mechanical energy stored in the third orthopedic implant 104 and tensions the third orthopedic implant 104 against the jaws 70-73 such that the jaws 70-73 in their engaged position and thus the implant insertion device 50 in its implant engagement position 42 constrain the third orthopedic implant 104 in its insertion shape 106.

While a third orthopedic implant 104 may be mechanically deformed from its unconstrained shape 105 to its insertion shape 106 before placement on the implant insertion device 50, in a second method, a third orthopedic implant 104 may be placed on the implant insertion device 50 in its unconstrained shape 105 and then mechanically deformed to its insertion shape 106 by the implant insertion device 50. Although not necessary, the third orthopedic implant 104 may be cooled prior to engagement with the implant insertion device 50 in order to place it in a martensitic state and aid in movement of the third orthopedic implant 104 from its unconstrained shape 105 to its insertion shape 106.

The implant insertion device 50 begins in its implant disengagement position 41 wherein the arms 58-61 reside in their normally open position and the jaws 70-73 reside in their disengaged position. The third orthopedic implant 104 in its unconstrained shape 105 is placed between the jaws 70-73 with its bridge 20 aligned with the bridge channel 86-89 of the jaws 70-73.

Once the third orthopedic implant 104 is placed between the jaws 70-73, the arms 58-61 and the jaws 70-73 are moved respectively from their normally open position to their closed position and from their disengaged position to their engaged position. In progressing from their disengaged position to their engaged position, the jaws 70-73 move angularly along an arc toward the central axis of the implant insertion device 50 when viewed at an end thereof and, due to their angled alignment interfaces 90-93, linearly away from the central axis of the implant insertion device 50 when viewed at a side thereof. The movement of the jaws 70-73 from their disengaged position to their engaged position places portions of the bridge 20 in the bridge channels 86-89 and contacts the leg interfaces 83 and 85 with a respective portion of the leg 6 and 7 and the leg interfaces 82 and 84 with a portion of the leg 5. In addition, the movement of the jaws 70-73 from their disengaged position to their engaged position and the resulting abutment of the leg interfaces 82-85 with respective portions of the legs 5-7 forces the third orthopedic implant 104 from its unconstrained shape 105 to its insertion shape 106, thereby storing mechanical energy in the third orthopedic implant 104. Progressing the slider 30 from its unclasped position to its clasped position frictionally engages its clasp 38 with the slider guides 74-77 thereby holding the jaws 70-73 in their engaged position. Securing the third orthopedic implant 104 between the jaws 70-73 maintains the mechanical energy stored in the third orthopedic implant 104 and tensions the third orthopedic implant 104 against the jaws 70-73 such that the jaws 70-73 in their engaged position and thus the implant insertion device 50 in its implant engagement position 42 constrain the third orthopedic implant 104 in its insertion shape 106.

After the third orthopedic implant 104 is secured with the implant insertion device 50, the third orthopedic implant 104 is ready for implantation into tissue or bones. The surgeon places the tips of the third orthopedic implant 104 into predrilled holes or the tips may be impacted into the tissue or bones thereby securing the third orthopedic implant 104 into the tissue or bones. Once the third orthopedic implant 104 is secured to the tissue or bones, it is ready for removal from the implant insertion device 50. To remove the third orthopedic implant 104 from the implant insertion device 50, the surgeon progresses the slider 30 within the arms 58-61 and along the slider receiver 53 from its clasped position to its clasped position. Moving the slider 30 from its clasped position to its unclasped position, disengages its clasp 38 from the slider guides 74-77 of the jaws 70-73 and releases the abutting relationship between the slider guides 74-75 and 76-77. As a consequence, the jaws 70-73 are released and thus are free to travel from their engaged position to their disengaged position while the arms 58-61 travel from their closed position to their normally open position. The jaws 70-73 accordingly disengage from the third orthopedic implant 104 in that the bridge interfaces 78-81 release the portions of the bridge 20 in their respective bridge channels 86-89 and the leg interfaces 83-85 release respectively the legs 5-7. When the jaws 70-73 are in their disengaged position, their leg interfaces 83-85 no longer abut respectively the legs 5-7 of the third orthopedic implant 104, resulting in the release of the tension between the third orthopedic implant 104 and the jaws 70-73 and a release of the third orthopedic implant 104 from the implant insertion device 50. In the event the third orthopedic implant 104 remains engaged with the jaws 70-73 after movement of the slider 30 to its unclasped position, the third orthopedic implant 104 may be removed from the implant insertion device 50 by applying a rotational force or by manually spreading the arms 58-61 or the jaws 70-73.

After the third orthopedic implant 104 is removed from the implant insertion device 50, the third orthopedic implant 104 is tamped down to fully engage the tissue or bone. Once fully engaged, the third orthopedic implant 104 attempts to move from its insertion shape 106 to its unconstrained shape 105, thereby releasing its mechanical energy into the tissue or bone. As the third orthopedic implant 104 moves from its insertion shape 106 to its unconstrained shape 105, the third orthopedic implant 104 places a constant force on the tissue or bones that fuses the tissue or bone together and aids the healing process.

The design of the implant insertion device 50 allows a gradual release of the third orthopedic implant 104. In particular, if the surgeon unclasps the slider 30 quickly, then the jaws 70-73 move from their engaged position to their disengaged position quickly thereby rapidly releasing the third orthopedic implant 104. Alternatively, if the surgeon believes a patient has poor bone quality, the surgeon can slowly unclasp the slider 30, which allows the jaws 70-73 to slowly move from their engaged position to their disengaged position thereby gradually releasing the third orthopedic implant 104.

Figure 27:
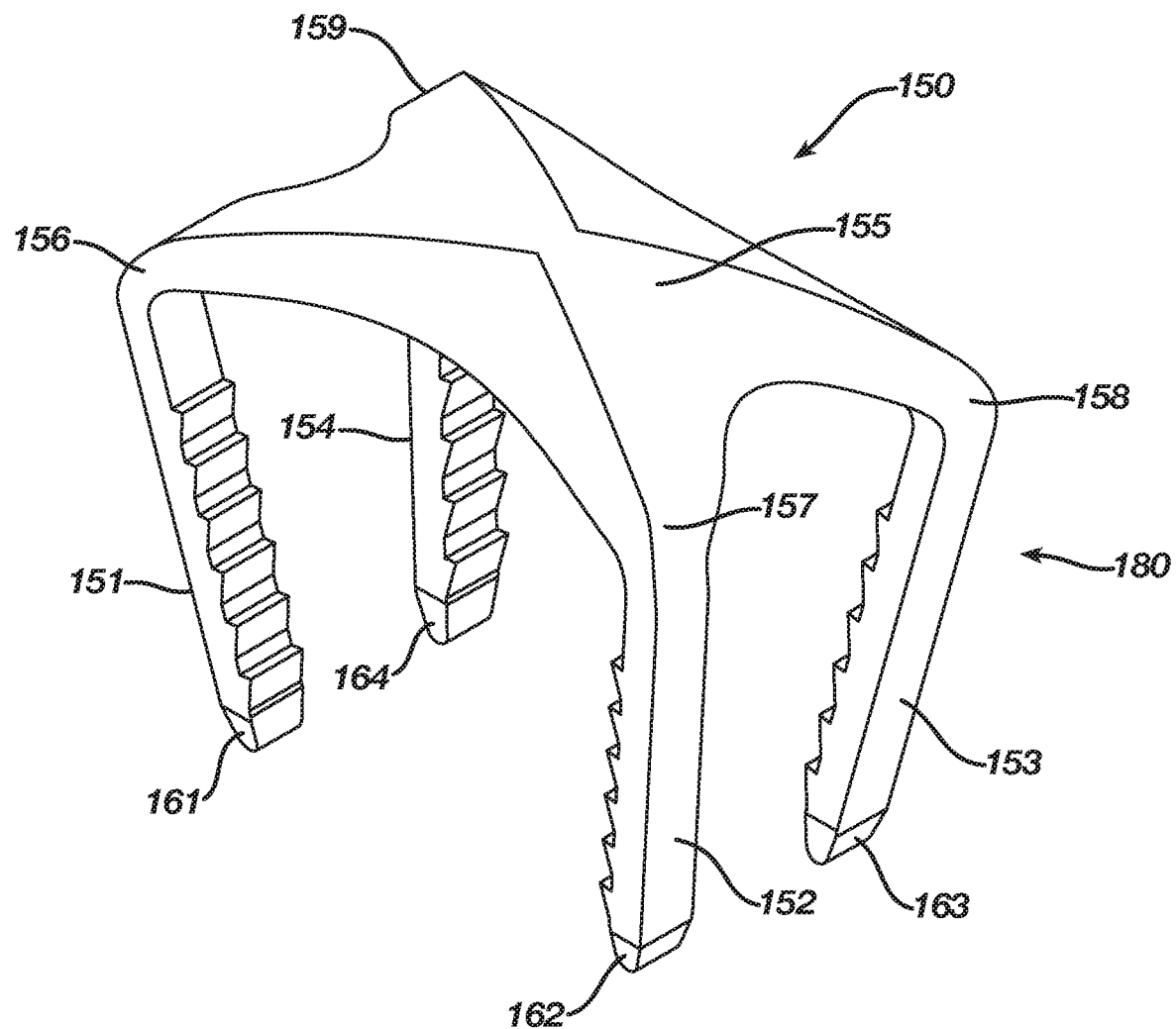
FIG. 27 is a perspective view illustrating a fourth implant in its unconstrained shape.
Figure 28:
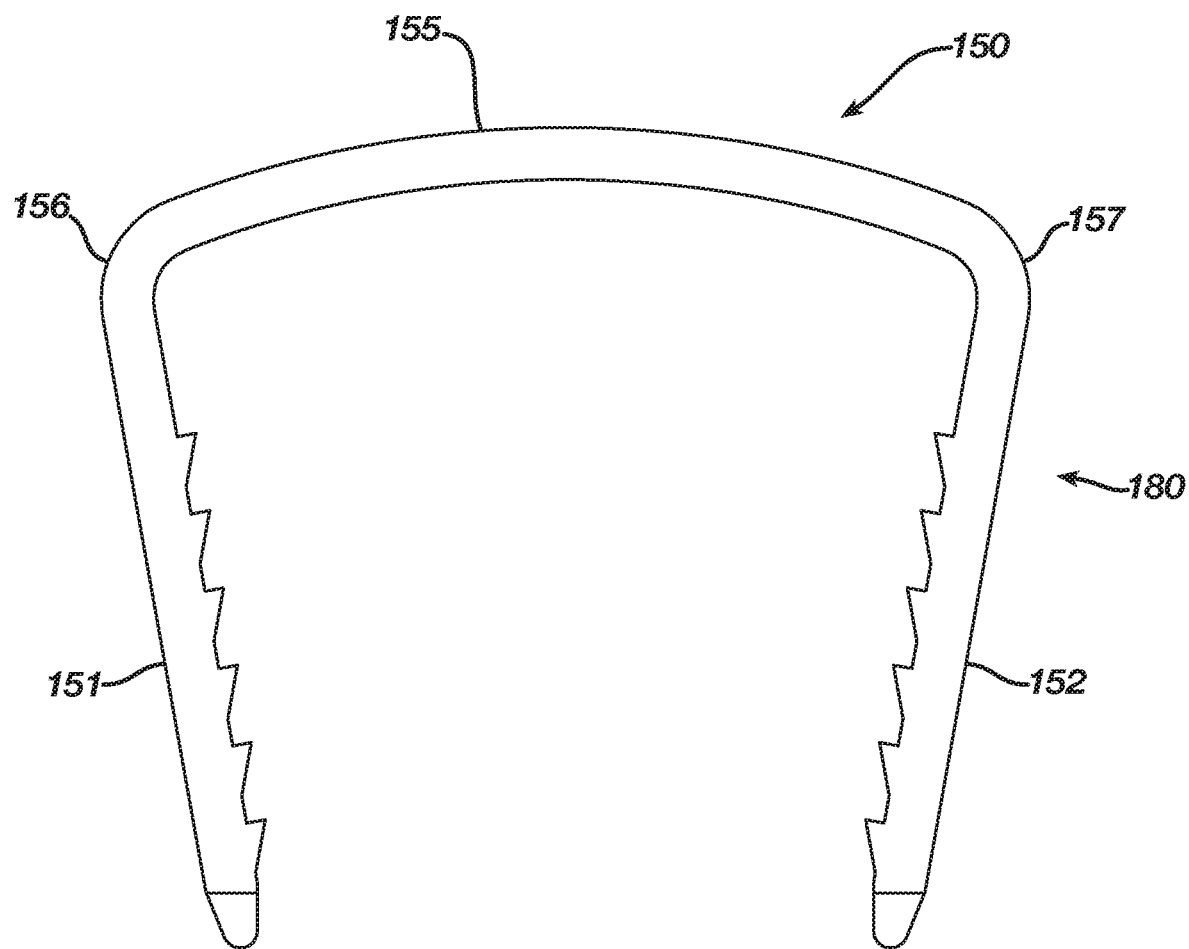
FIG. 28 is a side view illustrating the fourth implant in its unconstrained shape.

FIGS. 27 and 28 illustrate a fourth orthopedic implant 150 in an unconstrained shape 180. The fourth orthopedic implant 150 may be manufactured from any elastic material suitable for orthopedic use, such as a shape memory material (e.g., Nitinol). The fourth orthopedic implant 150 includes legs 151-154 connected by a bridge 155. The fourth orthopedic implant 150 includes corners 156-159 that connect a respective leg 151-154 with the bridge 155. Each leg 151-154 has a respective tip 161-164 that includes barbs thereon to improve the pull-out resistance of the fourth orthopedic implant 150. The unconstrained shape 180 where the legs 151-154 converge is the natural shape of the fourth orthopedic implant 150. Nevertheless, the fourth orthopedic implant 150 is deformable under the action of shape memory or superelasticity to an insertion shape 181 where the legs 151-154 reside substantially parallel and the corners 156-159 store energy. Since the insertion shape 181 is not the natural shape of the fourth orthopedic implant 150, the legs 151-154 must be mechanically constrained or the fourth orthopedic implant 150 must be chilled until it reaches its martensite phase whereby the legs 151-154 once deformed naturally remain in the insertion shape 181. Release of the mechanical restraint or the heating of the fourth orthopedic implant 150 to its austenite phase results in the fourth orthopedic implant 150 delivering the energy stored in the corners 156-159 such that the legs 151-154 exert a compressive force to tissue or bone after implantation. The fourth orthopedic implant 150 also may impart compression to tissue or bone from a bend in the bridge 155 that brings the legs 151 and 154 closer to the legs 152 and 153 as the fourth orthopedic implant 150 transitions from its insertion shape 181 to its unconstrained shape 180. While the fourth orthopedic implant 150 may be any implant with four legs, US Patent Publication No. US 20170065275A1 provides an example for the fourth orthopedic implant 150.

FIGS. 29-41 illustrate an implant insertion device 250 according to a second embodiment. The implant insertion device 250 as shown in FIGS. 29-41 engages a fourth orthopedic implant 150 and constrains the fourth orthopedic implant 150 in its insertion shape 181 such that a surgeon may insert the fourth orthopedic implant 150 into tissue or bone during surgery. Although the implant insertion device 250 will be described in combination with the fourth orthopedic implant 150, one of ordinary skill in the art will recognize that the implant insertion device 250 engages any suitable four-legged implant and constrains the implant in its insertion shape such that a surgeon may insert the implant into tissue or bone during surgery.

The implant insertion device 250 includes a body 251 and a slider 230 that moves between an unclasped position and a clasped position. The implant insertion device 250 resides in either an implant disengagement position 241 (shown in FIGS. 29, 31, and 33) or an implant engagement position 242 (shown in FIGS. 30, 32, and 34) and is movable therebetween. In the implant disengagement position 241, the fourth orthopedic implant 150 slips in or out of the implant insertion device 250 with no obstruction. In the implant engagement position 242, the implant insertion device 250 engages the fourth orthopedic implant 150 and maintains the fourth orthopedic implant 150 constrained in its insertion shape 181. In addition, the implant insertion device 250 allows a surgeon to manipulate the fourth orthopedic implant 150 and insert the fourth orthopedic implant 150 into tissue or bones requiring fixating.

The body 251 of the implant insertion device 250 includes a slider receiver 253, a first side 254, a second side 255, a handle 256 having a top 257, arms 258 and 259, and arms 260 and 261. A flat groove in both the first side 254 and the second side 255 of the body 251 defines the slider receiver 253 such that the slider receiver 253 receives a portion of the slider 230 to allow the securing of the slider 230 over the slider receiver 253 and thus to the body 251. The handle 256 provides a gripping surface on the first side 254 and the second side 255 of the body 251. The gripping surface of the handle 256 allows a surgeon to manipulate the implant insertion device 250 and therefore the fourth orthopedic implant 150 that is secured thereto. The arms 258 and 259 of the body 251 extend from the body 251 at the first side 254 and include a jaw 270 and a jaw 271, respectively. The arms 260 and 261 of the body 251 extend from the body 251 at the second side 255 and include a jaw 272 and a jaw 273, respectively. The arms 258-261 reside in a normally open position (shown in FIGS. 29, 31, and 33) whereby the arms 258-261 are spread apart and are movable to a closed position (shown in FIGS. 30, 32, and 34) whereby the arms 258-261 are adjacent. Movement of the arms 258-261 from their normally open position to their closed position progresses the jaws 270-273 from a disengaged position to an engaged position. The implant insertion device 250 may be manufactured from any suitable resilient material; however, in the first embodiment the implant insertion device 250 is made from plastic.

In the first embodiment, the body 251 of the implant insertion device 250 is manufactured in one piece using a mold. However, the body 251 of the implant insertion device 250 could be manufactured in two separate pieces. In particular, the arms 258 and 259, the jaws 270 and 271, and a portion of the handle 256 may form a first piece. The arms 260 and 261, the jaws 272 and 273, and a portion of the handle 256 may form a second piece. The two separate pieces are then fastened together using any suitable means such as a hinge or an adhesive to create the body 251.

The jaws 270-273 each include a slider guide 274-277, respectively, that interacts with the slider 230 as the slider 230 moves between its unclasped position to its clasped position. The jaws 270-273 each include a bridge interface 278-281, respectively, defining a bridge channel 286-289, respectively, that receives a portion of the bridge 155 therein. The jaws 270-273 each include a leg interface 282-285, respectively, that engages a portion of a leg 151-154, respectively, below the bridge 155. The jaws 270-273 each include an alignment interface 290-293, respectively, that interacts with an opposing alignment interface 290-293 during movement of the jaws 270-273 from their disengaged position (shown in FIGS. 29, 31, and 33) to their engaged position (shown in FIGS. 30, 32, and 34). The alignment interfaces 290 and 292 each include a leading edge 294 and a trailing edge 295 located in a plane offset relative to a plane of the leading edge 294 such that the alignment interfaces 290 and 291 angle across their faces from the leading edge 294 to the trailing edge 295. The alignment interfaces 291 and 293 each include a leading edge 296 and a trailing edge 297 located in a plane offset relative to a plane of the leading edge 296 such that the alignment interfaces 291 and 293 angle across their faces from the leading edge 297 to the trailing edge 297. In locating the trailing edges 295 of the alignment interfaces 290 and 292 offset relative to their leading edges 294 and the trailing edges 298 of the alignment interfaces 291 and 293 offset relative to their leading edges 296, the angles across the faces of the alignment interfaces 290 and 292 are complementary relative to the angles across the faces of the alignment interfaces 291 and 293.

The jaws 270-273 travel between their disengaged position and their engaged position to facilitate the securing of the fourth orthopedic implant 150 in the implant insertion device 250 as well as the removal of the fourth orthopedic implant 150 from the implant insertion device 250. As the implant insertion device 250, via manipulation of the arms 258-261 from their normally open position to their closed position, moves from its implant disengagement position 241 to its implant engagement position 242, the jaws 270-273 move angularly and linearly when progressing from their disengaged position to their engaged position. In particular, the jaws 270 and 271 move into abutting relationship at their alignment interfaces 290 and 291, and the jaws 272 and 273 move into abutting relationship at their alignment interfaces 292 and 293. In addition, the slider guide 274 moves into alignment adjacent with the slider guide 275 and the slider guide 276 moves into alignment adjacent with the slider guide 277 such that the slider guides 274-277 interact with the slider 230. The jaws 270-273 are complementary in shape and interact to form a unitary device in their engaged position that grasps the fourth orthopedic implant 150. The movement of the jaws 270-273 in engaging the fourth orthopedic implant 150 and constraining the fourth orthopedic implant 150 in its insertion shape 181 will be described more fully herein.

FIGS. 21-26 illustrate the slider 230. The slider 230 includes a clasp 238 having a clasping surface 231 and a clasping surface 232 that define a slot 239 therebetween. The slider 230 defines a slot 237 at a slider tail 234. The slider 230 further includes an actuator 233 having front faces 235 and back faces 236. The slot 237 allows the slider 230 to engage the body 251 and move between its unclasped and clasped positions. In particular, placement of the slider 230 within the body 251 by inserting the slider 230 between the arms 258-261 such that the slider 230 engages with the slider receiver 253 of the body 251 via the slot 237 secures the slider 230 with the body 251. The actuator 233 allows a user to operate the slider 230 by moving the slider 230 between its unclasped and its clasped position. Specifically, as shown in FIGS. 8 and 9, when a user pushes against the back faces 236 of the actuator 233, the slider 230 moves within the arms 258-261 and along the slider receiver 253 from its unclasped position to its clasped position. Conversely, when a user pulls against the front faces 235 of the actuator 233, the slider 230 moves within the arms 258-261 and along the slider receiver 253 from its clasped position to its unclasped position.

The clasp 238 of the slider 230 allows the slider 230 to hold the jay's 270-273 in their engaged position. Particularly, when the slider 230 moves from its unclasped position to its clasped position, the clasp 238 grasps the slider guides 274-277 in that the slider guides 274-277 enter the clasp 238 via its slot 239. More particularly, the clasping surface 231 frictionally engages the slider guides 274-275 and the clasping surface 232 frictionally engages the slider guides 276-277. The frictional engagement between the clasping surfaces 231 and 232 and slider guides 274-277, respectively, holds the jaws 270-273 in their engaged position.

Figure 29:
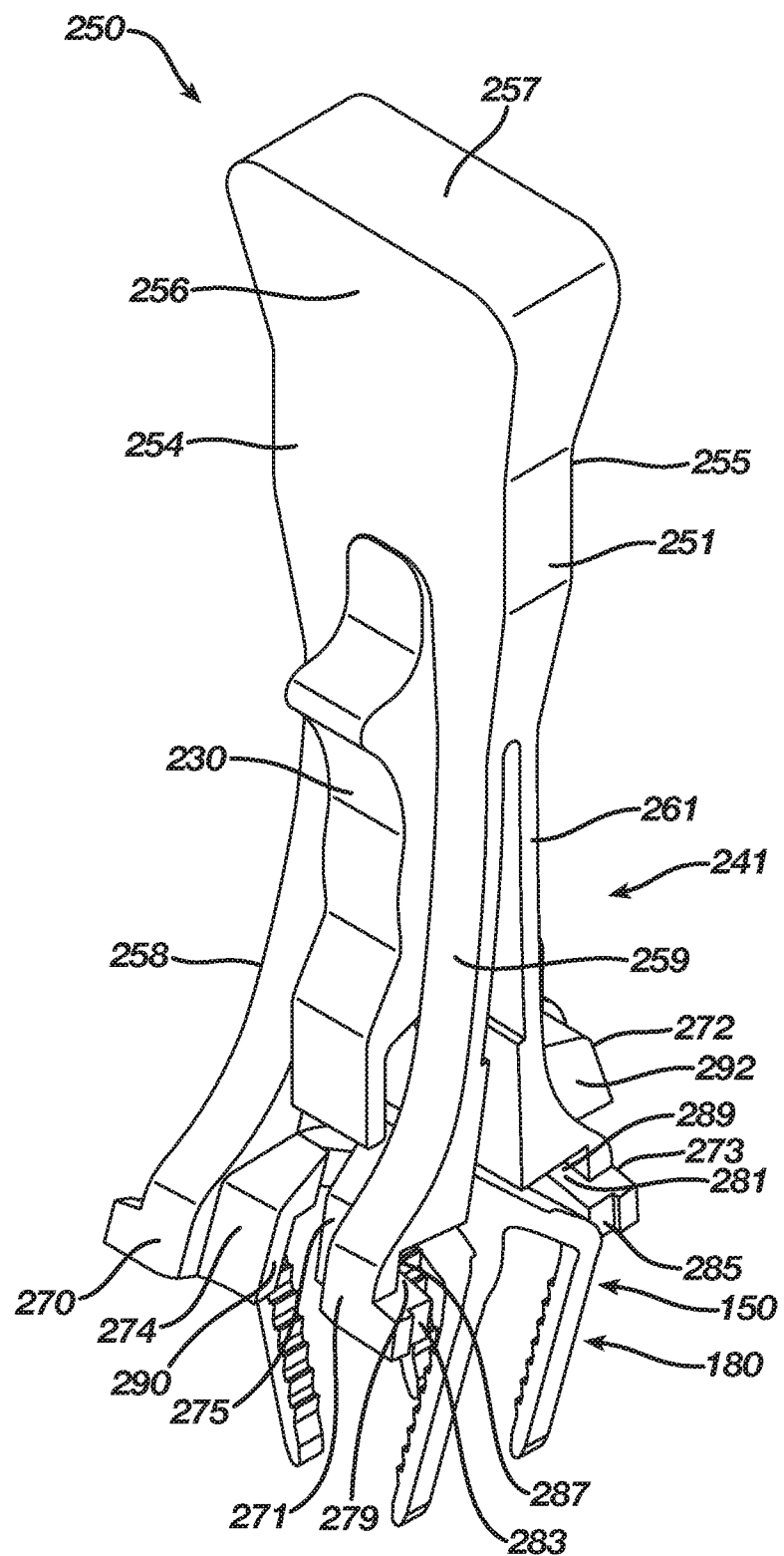
FIG. 29 is a perspective view illustrating the fourth implant and an implant insertion device according to a second embodiment in an implant disengagement position.
Figure 31:
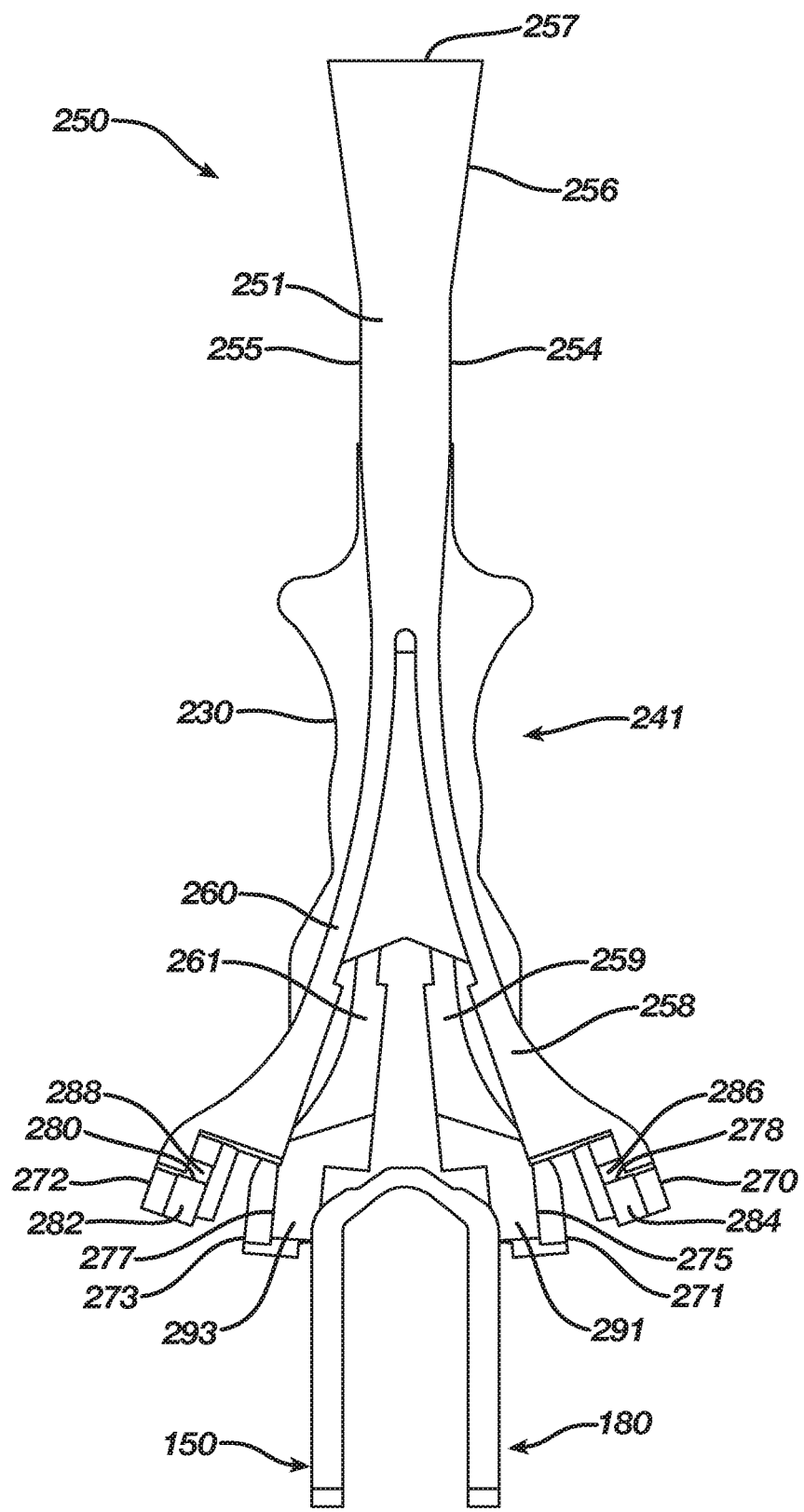
FIG. 31 is a rear view illustrating the fourth implant and the implant insertion device according to the second embodiment in its implant disengagement position.
Figure 33:
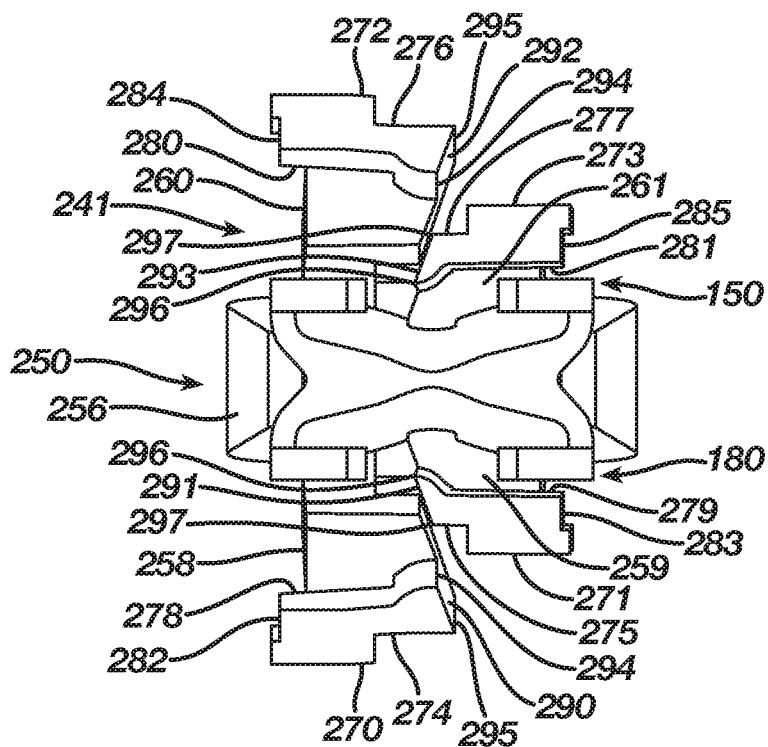
FIG. 33 is a bottom view illustrating the fourth implant and the implant insertion device according to the second embodiment in its implant disengagement position.
Figure 34:
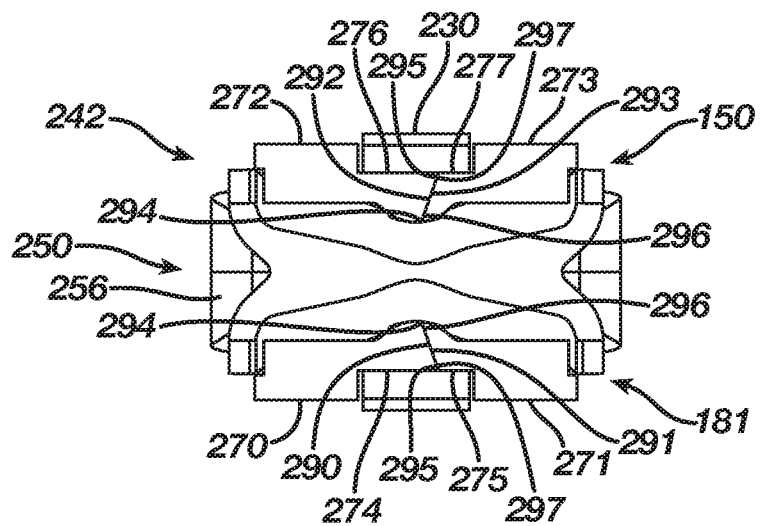
FIG. 34 is a bottom view illustrating the fourth implant and the implant insertion device according to the second embodiment in its implant engagement position.
Figure 35:
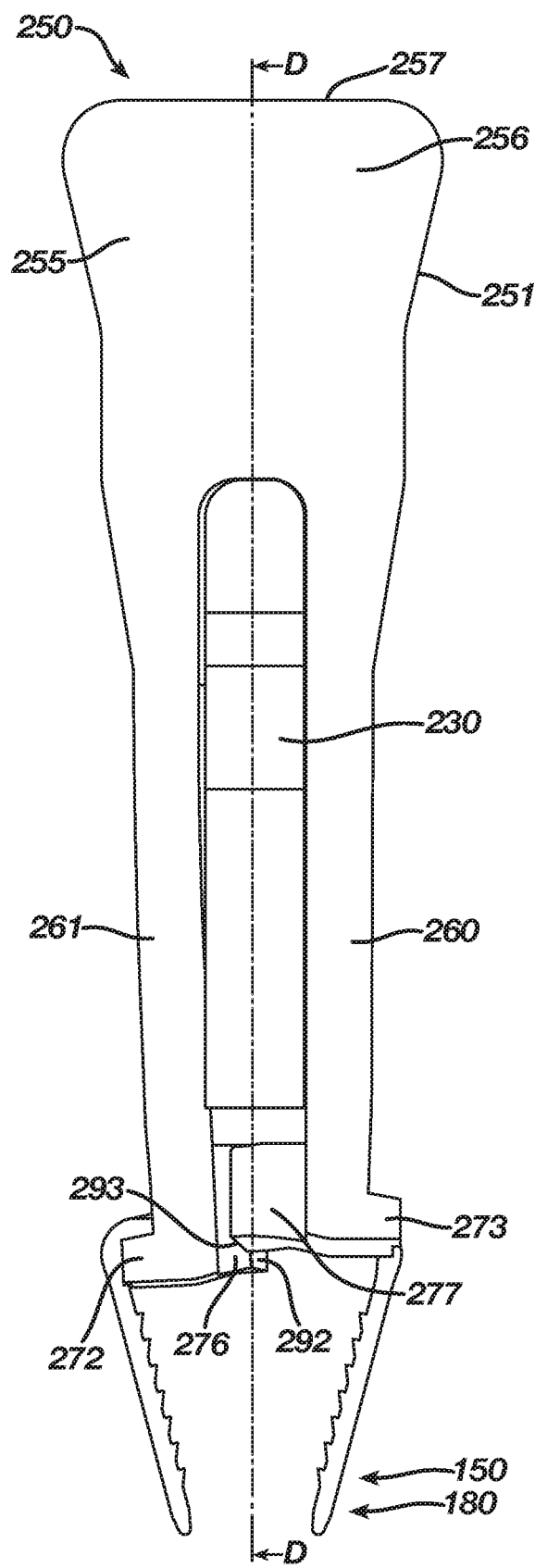
FIG. 35 is a side view illustrating the fourth implant and the implant insertion device according to the second embodiment in its implant disengagement position.
Figure 36:
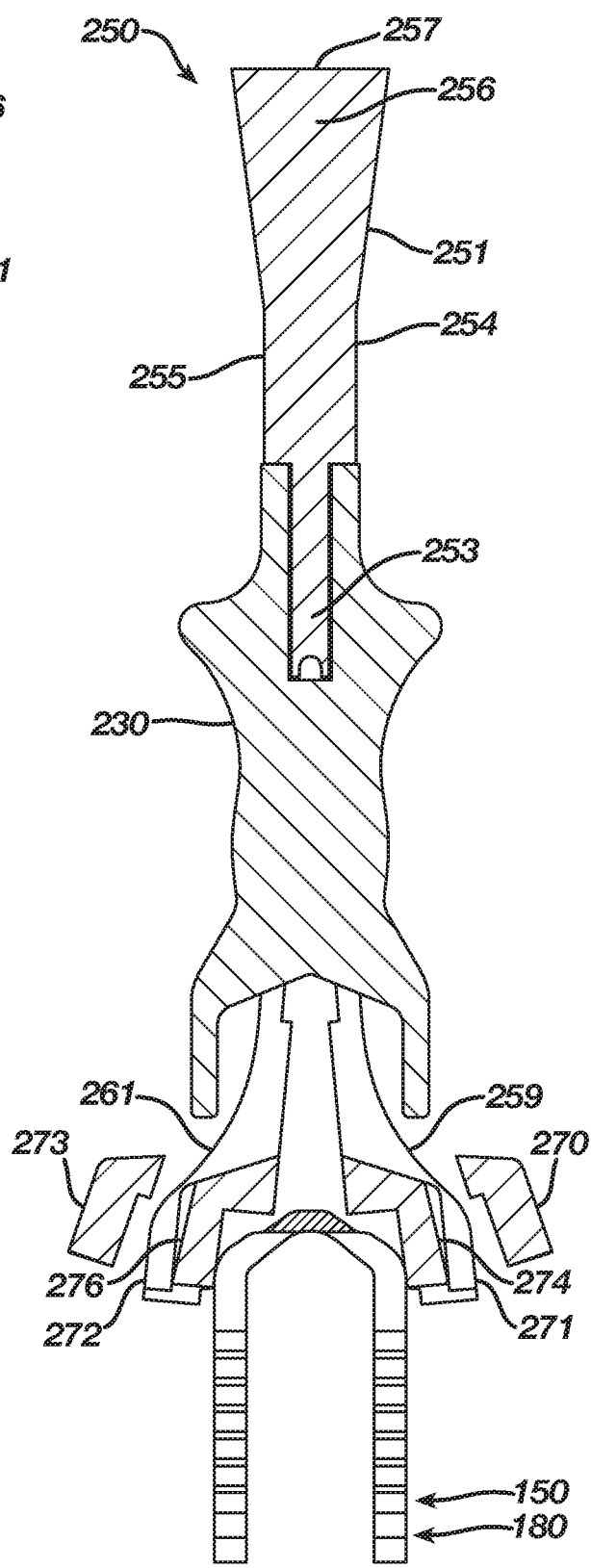
FIG. 36 is a cross-sectional view taken along lines D-D of FIG. 35 illustrating the fourth implant and the implant insertion device according to the second embodiment in its implant disengagement position.
Figure 37:
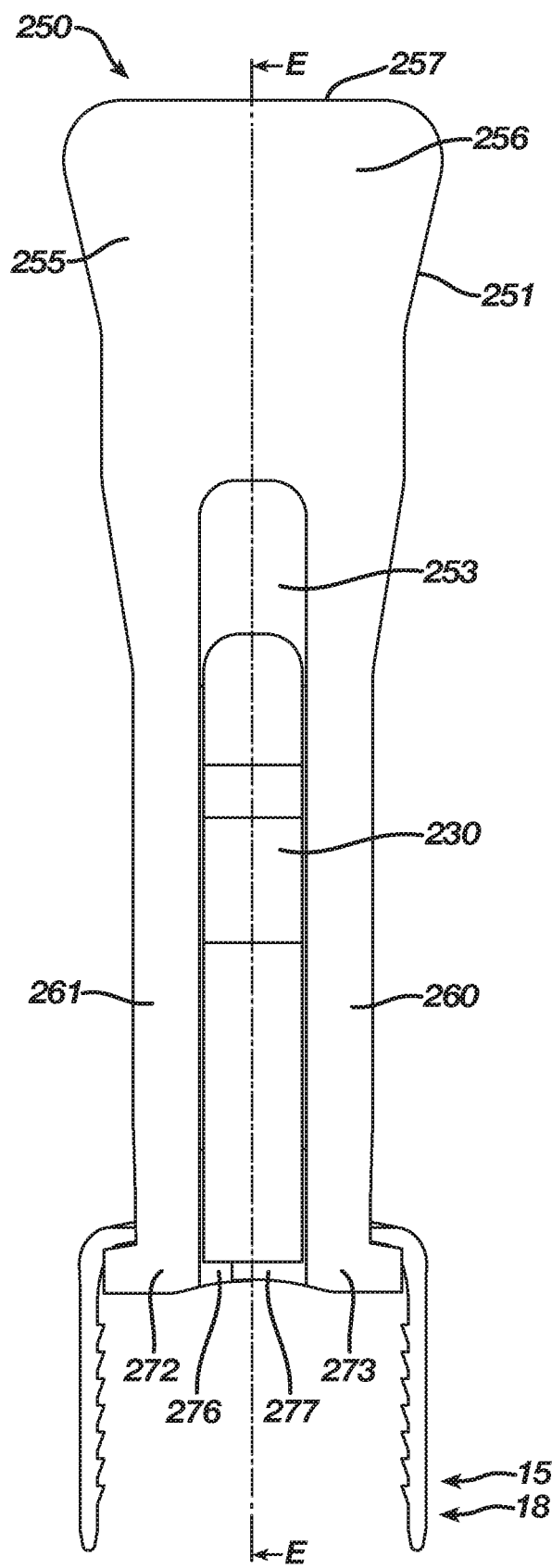
FIG. 37 is a side view illustrating the fourth implant and the implant insertion device according to the second embodiment in its implant engagement position.

The implant insertion device 250 according to the second embodiment prior its loading with a fourth orthopedic implant 150 begins in its implant disengagement position 241 illustrated in FIGS. 29, 31, and 33. In the implant disengagement position 241, the slider 230 resides in its unclasped position whereby the slider 230 is disengaged from the slider guides 274-277 such that the arms 258-261 are splayed in their normally open position and the jaws 270-273 are spread apart in their disengaged position. Referring specifically to FIGS. 29, 31, and 36, the arms 258-261 due to their construction from a resilient material reside at a first end angle relative to a central axis of the implant insertion device 250 when viewed at an end thereof. Furthermore, referring specifically to FIG. 35, the arms 258-261 due to their construction from a resilient material reside at a first side angle relative to a central axis of the implant insertion device 250 when viewed at a side thereof. Moreover, when the arms 258-261 reside at their first side angle, the leading edges 296 of the alignment interfaces 291 and 293, respectively, substantially align with the trailing edges 295 of the alignment interfaces 290 and 292 such that the leading edges 296 of the alignment interfaces 291 and 293 are located in a plane offset relative to a plane of the leading edges 294 for the alignment interfaces 290 and 292.

When loading the implant insertion device 250, a fourth orthopedic implant 150 in its unconstrained shape 180 is located between the jaws 270-273 with its bridge 155 aligned with the bridge channels 286-289 of the jaws 270-273. The implant insertion device 250 progresses from its implant disengagement position 241 to its engagement position 242 such that the arms 258-261 move to their closed position and the jaws 270-273 contact the fourth orthopedic implant 150 and manipulate the fourth orthopedic implant 150 to its insertion shape 181 as the jaws 270-273 travel from their disengaged position to their engaged position. The slider 230 moves from its unclasped position to its clasped position whereby the slider 230 engages the slider guides 274-277 to hold the arms 258-261 in their closed position and the jaws 270-273 in their engaged position that constrains the fourth orthopedic implant 150 in its insertion shape 181.

Alternatively, a fourth orthopedic implant 150 manipulated to its insertion shape 181 and held therein is located between the jaws 270-273 with its bridge 155 aligned with the bridge channels 286-289 of the jaws 270-273. The implant insertion device 250 progresses from its implant disengagement position 241 to its engagement position 242 such that the arms 258-261 move to their closed position and the jaws 270-273 contact the fourth orthopedic implant 150 as the jaws 270-273 travel from their disengaged position to their engaged position. The slider 230 moves from its unclasped position to its clasped position whereby the slider 230 engages the slider guides 274-277 to hold the arms 258-261 in their closed position and the jaws 270-273 in their engaged position that constrains the fourth orthopedic implant 150 in its insertion shape 181.

Figure 30:
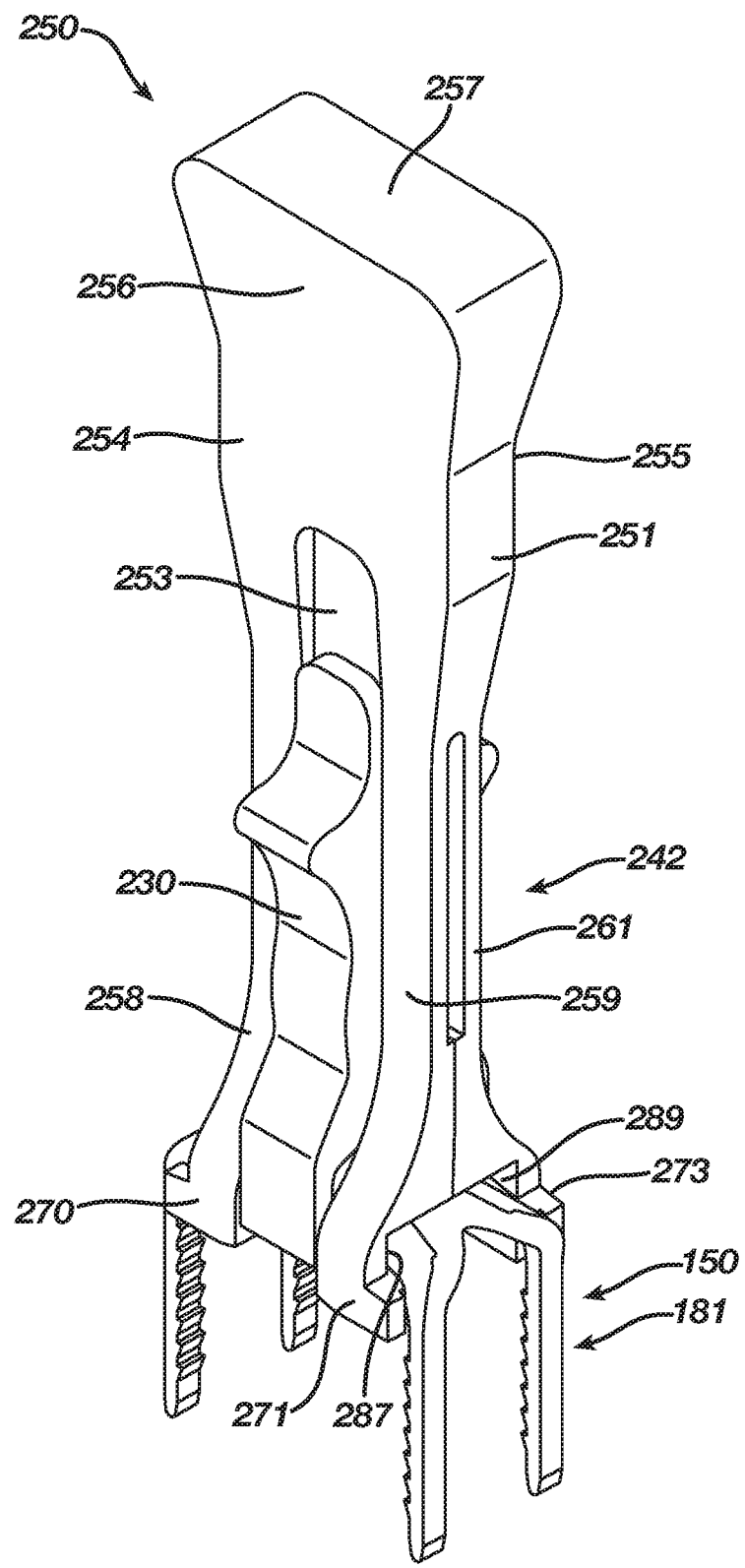
FIG. 30 is a perspective view illustrating the fourth implant and the implant insertion device according to the second embodiment in an implant engagement position.
Figure 32:
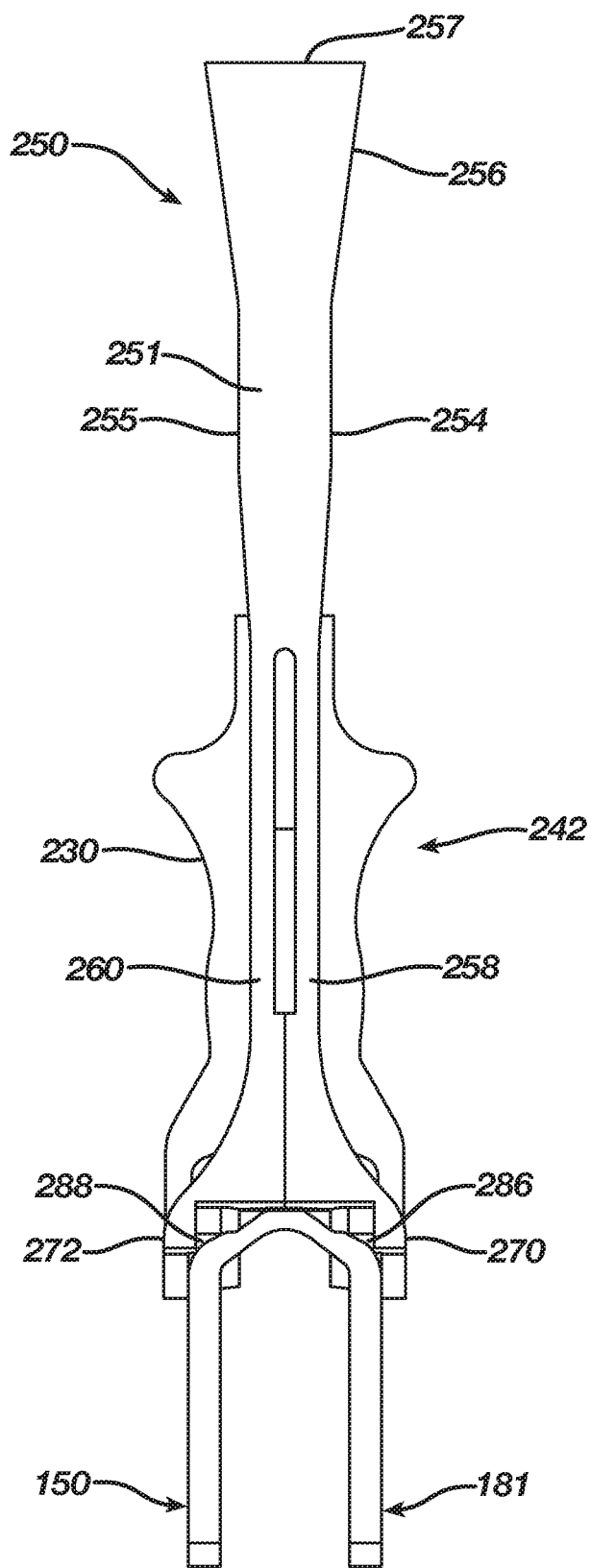
FIG. 32 is a rear view illustrating the fourth implant and the implant insertion device according to the second embodiment in its implant engagement position.
Figure 38:
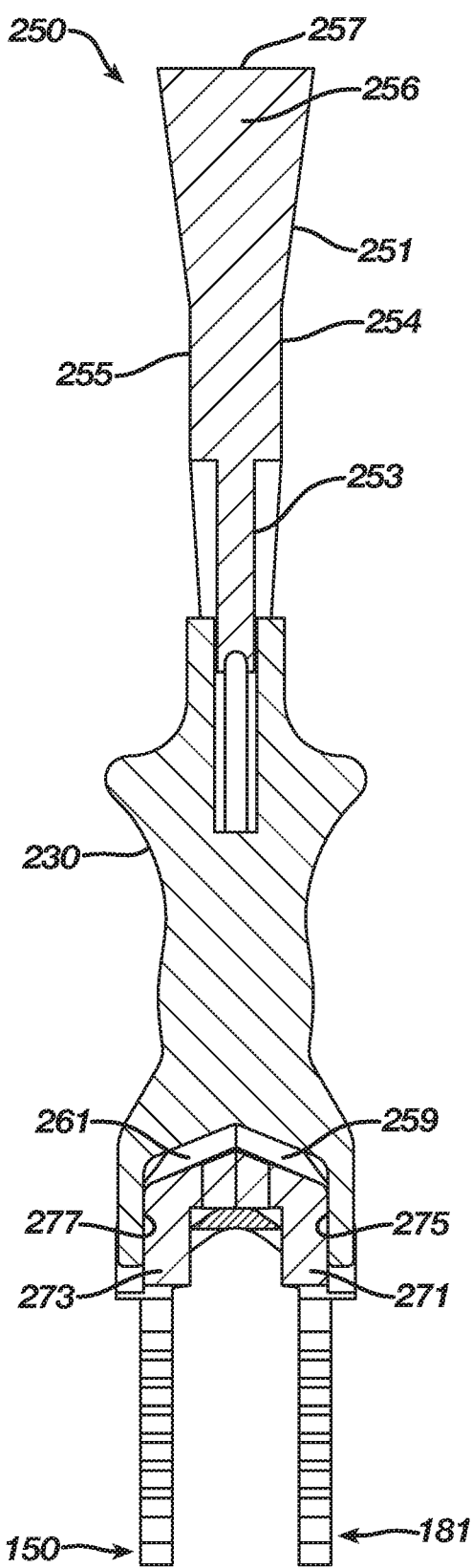
FIG. 38 is a cross-sectional view taken along lines E-E of FIG. 37 illustrating the fourth implant and the implant insertion device according to the second embodiment in its implant engagement position.
Figure 39:
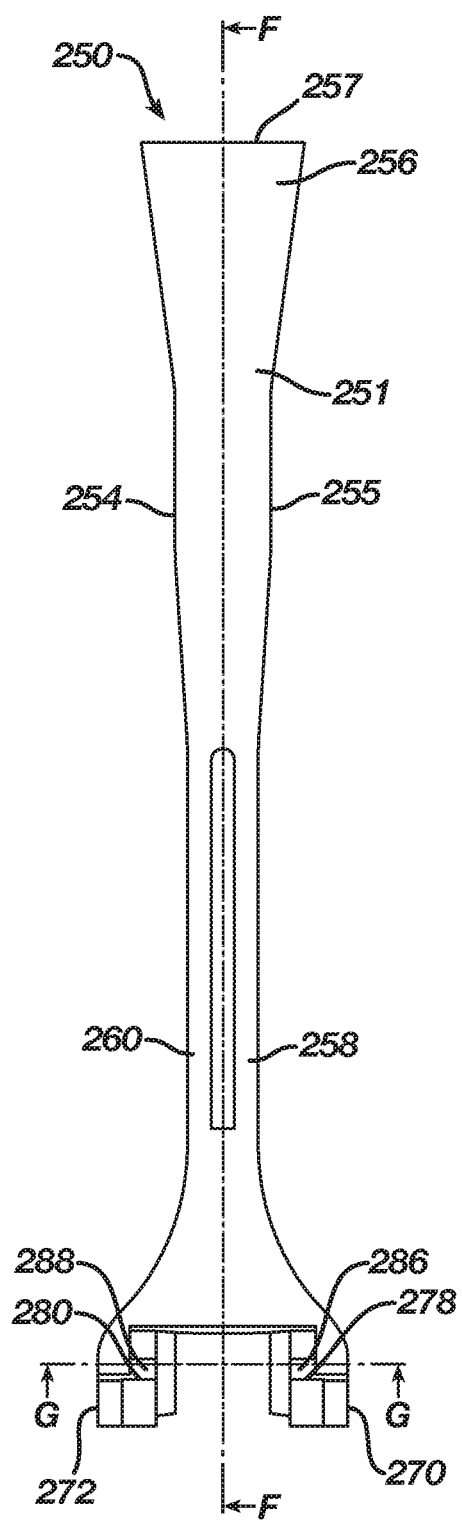
FIG. 39 is a rear view illustrating the implant insertion device according to the second embodiment in its implant engagement position.
Figure 40:
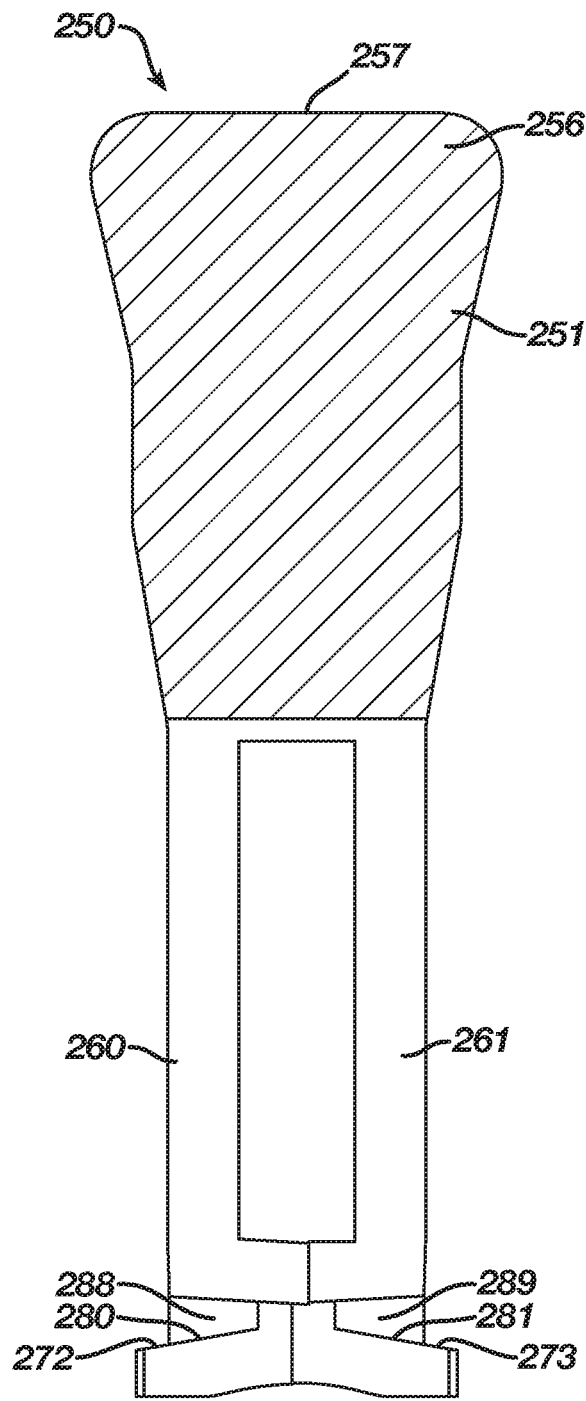
FIG. 40 is a cross-sectional view taken along lines F-F of FIG. 39 illustrating the implant insertion device according to the second embodiment in its implant engagement position.
Figure 41:
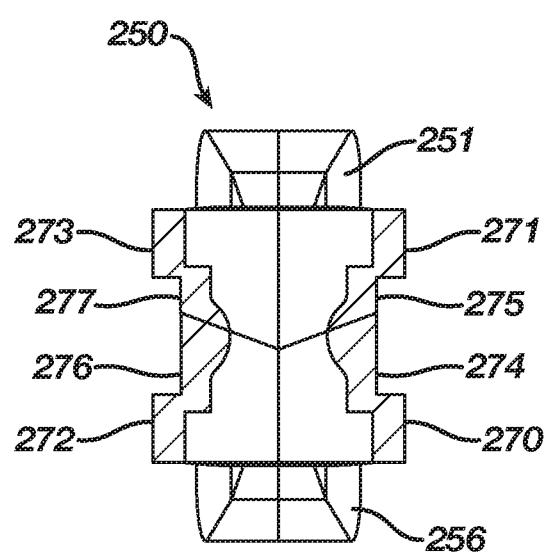
FIG. 41 is a cross-sectional view taken along lines G-G of FIG. 39 illustrating the implant insertion device according to the second embodiment in its implant engagement position.
Figure 42:
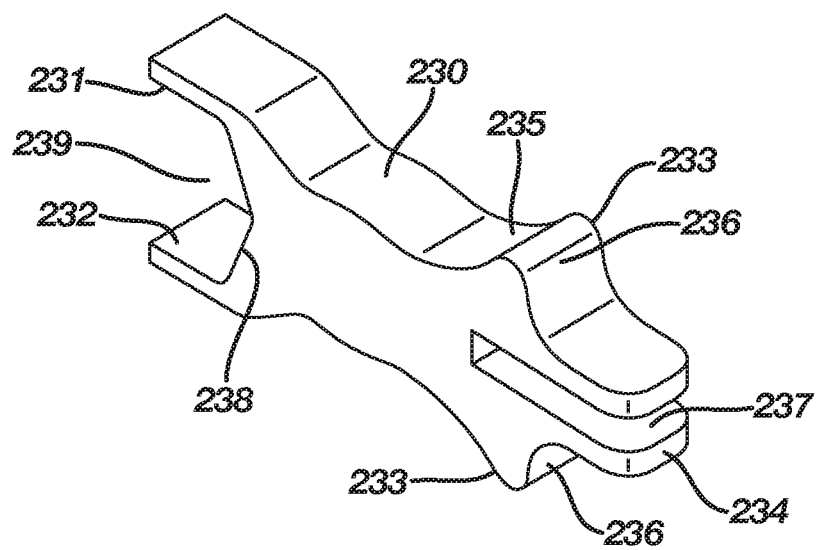
FIG. 42 is a perspective view illustrating a slider of the implant insertion device according to the second embodiment.
Figure 44:
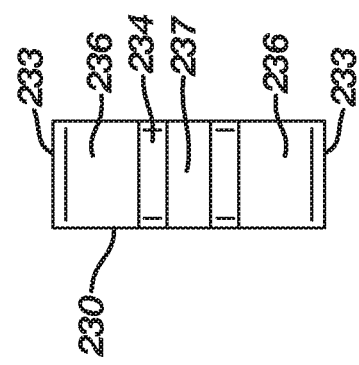
FIG. 44 is a right side view illustrating the slider of the implant insertion device according to the second embodiment.
Figure 46:
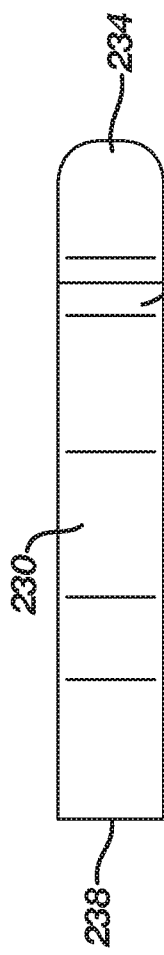
FIG. 46 is a top view illustrating the slider of the implant insertion device according to the second embodiment.
Figure 43:
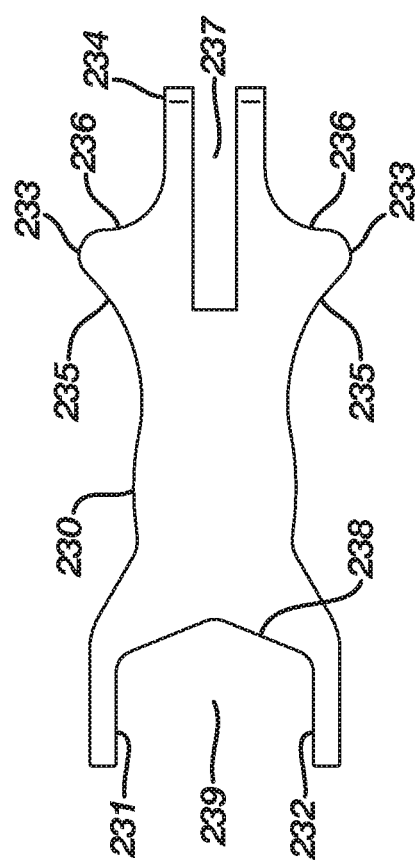
FIG. 43 is a front view illustrating the slider of the implant insertion device according to the second embodiment.
Figure 47:
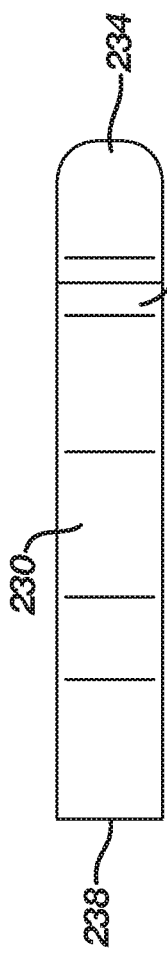
FIG. 47 is a bottom view illustrating the slider of the implant insertion device according to the second embodiment.
Figure 45:
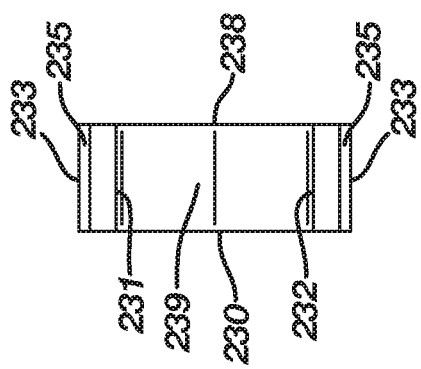
FIG. 45 is a left side view illustrating the slider of the implant insertion device according to the second embodiment.

Referring specifically to FIGS. 30, 32, and 38, the arms 258-261 due to their construction from a resilient material move along an arc toward the central axis of the implant insertion device 250 when viewed at an end thereof from the first end angle to a second end angle which is less than the first end angle. In the first embodiment, the first end angle is any angle greater than 0° relative to the central axis of the implant insertion device 250 when viewed at an end thereof that allows insertion of a fourth orthopedic implant 150 in its unconstrained shape 180 between the jaws 270-273, and the second end angle is substantially equal to 0° relative to a central axis of the implant insertion device 250 when viewed at an end thereof. Furthermore, referring specifically to FIG. 37, the arms 258-261 due to their construction from a resilient material move along an arc away from the central axis of the implant insertion device 250 when viewed at a side thereof from the first side angle to a second side angle which is less than the first side angle. In the first embodiment, the first side angle is any angle greater than 0° relative to the central axis of the implant insertion device 250 when viewed at a side thereof that allows insertion of a fourth orthopedic implant 150 in its unconstrained shape 180 between the jaws 270-273, and the second end angle is substantially equal to 0° relative to the central axis of the implant insertion device 250 when viewed at a side thereof.

When loading the implant insertion device 250 with a fourth orthopedic implant 150 in its unconstrained shape 180, movement of the arms 258-261 from their normally open position to their closed position and the jaws 270-273 from their disengaged position to their engaged position contacts the bridge interface 278 with a portion of the bridge 155 adjacent the corner 156 and inserts the portion into the bridge channel 286, the bridge interface 279 with a portion of the bridge 155 adjacent the corner 157 and inserts the portion into the bridge channel 287, the bridge interface 280 with a portion of the bridge 155 adjacent the corner 159 and inserts the portion into the bridge channel 288, and the bridge interface 281 with a portion of the bridge 155 adjacent the corner 158 and inserts the portion into the bridge channel 289. In addition, the leg interface 282 contacts a portion of the leg 151 below the corner 156, the leg interface 283 contacts a portion of the leg 152 below the corner 157, the leg interface 284 contacts a portion of the leg 154 below the corner 159, and the leg interface 285 contacts a portion of the leg 153 below the corner 158. When moved to their closed position, the arms 258-261 travel along an arc toward the central axis of the implant insertion device 250 when viewed at an end thereof from the first end angle shown in FIG. 31 to the second end angle shown in FIG. 32.

Progression of the jaws 270-273 from their disengaged position to their engaged position begins with the leading edges 296 of the alignment interfaces 291 and 293 contacting the trailing edges 295 of the alignment interfaces 290 and 292 and ends when the leading edges 296 and trailing edges 297 of the alignment interfaces 291 and 293 respectively reside adjacent the leading edges 294 and trailing edges 295 of the alignment interfaces 290 and 292 such that the alignment interfaces 291 and 293 abut their respective alignment interfaces 290 and 291. The offset of the trailing edges 295 and 297 respectively relative to the leading edges 294 and 296 and the resulting complementary angled faces of the alignment interfaces 290-291 and 292-293 facilitate movement of the arms 258-261 from their normally open position to their closed position as the alignment interfaces 291 and 293 travel into an abutting relationship with the alignment interfaces 290 and 292 because the complementary angled faces of the alignment interfaces 290-291 displace the jaw 270 linearly relative to the jaw 271 and the complementary angled faces of the alignment interfaces 292-293 displace the jaw 272 linearly relative to the jaw 273. Specifically, the jaws 270 and 271 and the jaws 272 and 273 move in opposing linear directions such that the jaw 270 engages the leg 151 at its leg interface 282, the jaw 271 engages the leg 152 at its leg interface 283, and the jaw 272 engages the leg 154 at its the leg interface 284, and the jaw 273 engages the leg 153 at its leg interface 285. The opposing linear motion of the jaw 270 relative to the jaw 271 and the jaw 272 relative to the jaw 273 produces movement of the arms 258-261 along an arc away from the central axis of the implant insertion device 250 when viewed at a side thereof from their first side angle shown in FIG. 35 to their second side angle shown in FIG. 37. Moreover, the opposing linear motion of the jaw 270 relative to the jaw 271 and the jaw 272 relative to the jaw 273 progresses a fourth orthopedic implant 150 from its unconstrained shape 180 to its insertion shape 181 and further constrains the fourth orthopedic implant 150 in its insertion shape 181. Alternatively, when a fourth orthopedic implant 150 was previously manipulated to its insertion shape 181 and held therein, the opposing linear motion of the jaw 270 relative to the jaw 271 and the jaw 272 relative to the jaw 273 constrains the fourth orthopedic implant 150 in its insertion shape 181.

Movement of the arms 258-261 from their normally open position to their closed position and the jaws 270-273 from their disengaged position to their engaged position further progresses the slider guide 274 into alignment adjacent with the slider guide 275 and the slider guide 276 into alignment adjacent with the slider guide 277. Once the slider guides 274 and 276 reside in alignment with their respective slider guides 275 and 277, the slider 230 moves within the arms 258-261 and along the slider receiver 253 from its unclasped position to its clasped position. In particular, the clasp 238 of the slider 230 slides over the slider guides 274-277 such that the clasping surface 231 frictionally engages the slider guides 274 and 275 and the clasping surface 32 frictionally engages the slider guides 276 and 277. The frictional engagement between the clasping surfaces 231 and 232 and slider guides 274-277, respectively, holds the jaws 270-273 in their engaged position. The jaws 270-273 in their engaged position are unitary in that portions of the bridge 155 reside in the bridge channels 286-289 while the leg interfaces 282-285 abut a respective portion of the legs 151-154 whereby the closed jaws 270-273 and thus the implant insertion device 250 constrain a fourth orthopedic implant 150 in its insertion shape 181.

In a first method to receive a fourth orthopedic implant 150, the implant insertion device 250 begins in its implant disengagement position 241 wherein the arms 258-261 reside in their normally open position and the jaws 270-273 reside in their disengaged position. The fourth orthopedic implant 150 is mechanically deformed from its unconstrained shape 180 into its insertion shape 181 such that the fourth orthopedic implant 150 stores mechanical energy. After being mechanically deformed from its unconstrained shape 180 to its insertion shape 181, the fourth orthopedic implant 150 is placed between the jaws 270-273 with its bridge 155 aligned with the bridge channel 286-289 of the jaws 270-273.

Once the fourth orthopedic implant 150 is placed between the jaws 270-273, the arms 258-261 and the jaws 270-273 are moved respectively from their normally open position to their closed position and from their disengaged position to their engaged position. In progressing from their disengaged position to their engaged position, the jaws 270-273 move angularly along an arc toward the central axis of the implant insertion device 250 when viewed at an end thereof and, due to their angled alignment interfaces 290-293, linearly away from the central axis of the implant insertion device 250 when viewed at a side thereof. The movement of the jaws 270-273 from their disengaged position to their engaged position places portions of the bridge 155 in the bridge channels 286-289 and abuts the leg interfaces 282-285 with a respective portion of the legs 151-154. Progressing the slider 230 from its unclasped position to its clasped position frictionally engages its clasp 238 with the slider guides 274-277 thereby holding the jaws 270-273 in their engaged position. Securing the fourth orthopedic implant 150 between the jaws 270-273 maintains the mechanical energy stored in the fourth orthopedic implant 150 and tensions the fourth orthopedic implant 150 against the jaws 270-273 such that the jaws 270-273 in their engaged position and thus the implant insertion device 250 in its implant engagement position 242 constrain the fourth orthopedic implant 150 in its insertion shape 181.

While a fourth orthopedic implant 150 may be mechanically deformed from its unconstrained shape 180 to its insertion shape 181 before placement on the implant insertion device 250, in a second method, a fourth orthopedic implant 150 may be placed on the implant insertion device 250 in its unconstrained shape 180 and then mechanically deformed to its insertion shape 181 by the implant insertion device 250. Although not necessary, the fourth orthopedic implant 150 may be cooled prior to engagement with the implant insertion device 250 in order to place it in a martensitic state and aid in movement of the fourth orthopedic implant 150 from its unconstrained shape 180 to its insertion shape 181.

The implant insertion device 250 begins in its implant disengagement position 241 wherein the arms 258-261 reside in their normally open position and the jaws 270-273 reside in their disengaged position. The fourth orthopedic implant 150 in its unconstrained shape 180 is placed between the jaws 70-73 with its bridge 155 aligned with the bridge channel 286-289 of the jaws 270-273.

Once the fourth orthopedic implant 150 is placed between the jaws 270-273, the arms 258-261 and the jaws 270-273 are moved respectively from their normally open position to their closed position and from their disengaged position to their engaged position. In progressing from their disengaged position to their engaged position, the jaws 270-273 move angularly along an arc toward the central axis of the implant insertion device 250 when viewed at an end thereof and, due to their angled alignment interfaces 290-293, linearly away from the central axis of the implant insertion device 250 when viewed at a side thereof. The movement of the jaws 270-273 from their disengaged position to their engaged position places portions of the bridge 155 in the bridge channels 286-289 and contacts the leg interfaces 282-285 with a respective portion of the legs 151-154. In addition, the movement of the jaws 270-273 from their disengaged position to their engaged position and the resulting abutment of the leg interfaces 282-285 with respective portions of the legs 151-154 forces the fourth orthopedic implant 150 from its unconstrained shape 180 to its insertion shape 181, thereby storing mechanical energy in the fourth orthopedic implant 150. Progressing the slider 230 from its unclasped position to its clasped position frictionally engages its clasp 238 with the slider guides 274-277 thereby holding the jaws 270-273 in their engaged position. Securing the fourth orthopedic implant 150 between the jaws 270-273 maintains the mechanical energy stored in the fourth orthopedic implant 150 and tensions the fourth orthopedic implant 150 against the jaws 270-273 such that the jaws 270-273 in their engaged position and thus the implant insertion device 250 in its implant engagement position 242 constrain the fourth orthopedic implant 150 in its insertion shape 181.

After the fourth orthopedic implant 150 is secured with the implant insertion device 250, the fourth orthopedic implant 150 is ready for implantation into tissue or bones. The surgeon places the tips of the fourth orthopedic implant 150 into predrilled holes or the tips may be impacted into the tissue or bones thereby securing the fourth orthopedic implant 150 into the tissue or bones. Once the fourth orthopedic implant 150 is secured to the tissue or bones, it is ready for removal from the implant insertion device 250. To remove the fourth orthopedic implant 150 from the implant insertion device 250, the surgeon progresses the slider 230 within the arms 258-261 and along the slider receiver 253 from its clasped position to its clasped position. Moving the slider 230 from its clasped position to its unclasped position, disengages its clasp 238 from the slider guides 274-277 of the jaws 270-273 and releases the slider guides 274-277. As a consequence, the jaws 270-273 are released and thus are free to travel from their engaged position to their disengaged position while the arms 258-261 travel from their closed position to their normally open position. The jaws 270-273 accordingly disengage from the fourth orthopedic implant 150 in that the bridge interfaces 278-281 release the portions of the bridge 155 in their respective bridge channels 286-289 and the leg interfaces 283-285 release respectively the legs 151-154. When the jaws 270-273 are in their disengaged position, their leg interfaces 283-285 no longer abut respectively the legs 151-154 of the fourth orthopedic implant 150, resulting in the release of the tension between the fourth orthopedic implant 150 and the jaws 270-273 and a release of the fourth orthopedic implant 150 from the implant insertion device 250. In the event the fourth orthopedic implant 150 remains engaged with the jaws 270-273 after movement of the slider 230 to its unclasped position, the fourth orthopedic implant 150 may be removed from the implant insertion device 250 by applying a rotational force or by manually spreading the arms 258-261 or the jaws 270-273.

After the fourth orthopedic implant 150 is removed from the implant insertion device 250, the fourth orthopedic implant 150 is tamped down to fully engage the tissue or bone. Once fully engaged, the fourth orthopedic implant 150 attempts to move from its insertion shape 181 to its unconstrained shape 180, thereby releasing its mechanical energy into the tissue or bone. As the fourth orthopedic implant 150 moves from its insertion shape 181 to its unconstrained shape 180, the fourth orthopedic implant 150 places a constant force on the tissue or bones that fuses the tissue or bone together and aids the healing process.

The design of the implant insertion device 250 allows a gradual release of the fourth orthopedic implant 150. In particular, if the surgeon unclasps the slider 230 quickly, then the jaws 270-273 move from their engaged position to their disengaged position quickly thereby rapidly releasing the fourth orthopedic implant 150. Alternatively, if the surgeon believes a patient has poor bone quality, the surgeon can slowly unclasp the slider 230, which allows the jaws 270-273 to slowly move from their engaged position to their disengaged position thereby gradually releasing the fourth orthopedic implant 150.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An implant insertion device adapted for use with a shape memory implant movable between an unconstrained shape and an insertion shape, whereby the implant insertion device maintains the shape memory implant in the insertion shape until a delivery of the shape memory implant into tissue or bone, the implant insertion device, comprising:
   a body, comprising:
      a first jaw adapted to engage the shape memory implant,
      a second jaw adapted to engage the shape memory implant,
      a third jaw adapted to engage the shape memory implant, and
      a fourth jaw adapted to engage the shape memory implant, wherein the first jaw, the second jaw, the third jaw, and the fourth jaw are movable from a disengaged position to an engaged position;
   a slider coupled with the body, wherein the slider is movable between an unclasped position and a clasped position, further wherein the slider in the clasped position maintains the first jaw, the second jaw, the third jaw, and the fourth jaw in the engaged position;
   the first jaw resides in opposed relationship with the second jaw, the first jaw and the second jaw including alignment interfaces having complementary angled faces, whereby progression of the first jaw and the second jaw from the disengaged position to the engaged position moves the alignment interfaces into an abutting relationship, further whereby the alignment interfaces due to the complementary angled faces move the first jaw and the second jaw in opposing linear directions such that the first jaw and the second jaw are adapted to engage the shape memory implant and maintain the shape memory implant in the insertion shape; and
   the third jaw resides in opposed relationship with the fourth jaw, the third jaw and the fourth jaw including alignment interfaces having complementary angled faces, whereby progression of the third jaw and the fourth jaw to the engaged position moves the alignment interfaces into an abutting relationship, further whereby the alignment interfaces due to the complementary angled faces move the third jaw and the fourth jaw in opposing linear directions such that the third jaw and the fourth jaw are adapted to engage the shape memory implant and maintain the shape memory implant in the insertion shape.

2. The implant insertion device according to claim 1, wherein the body, further comprises:
   a first arm, wherein the first jaw resides at the termination of the first arm;
   a second arm, wherein the second jaw resides at the termination of the second arm;
   a third arm, wherein the third jaw resides at the termination of the third arm; and
   a fourth arm, wherein the fourth jaw resides at the termination of the fourth arm.

3. The implant insertion device according to claim 2, wherein the first arm, the second arm, the third arm, and the fourth arm include a splayed open position that spreads apart the first jaw, the second jaw, the third jaw, and the fourth jaw in the disengaged position, further wherein the first arm, the second arm, the third arm, and the fourth arm are movable from the splayed open position to a closed position that places the first jaw, the second jaw, the third jaw, and the fourth jaw in the engaged position.

4. The implant insertion device according to claim 3, wherein, when the first arm, the second arm, the third arm, and the fourth arm move from the splayed open position to the closed position, the first arm, the second arm, the third arm, and the fourth arm travel along an arc toward a central axis of the body such that the first jaw, the second jaw, the third jaw, and the fourth jaw move angularly to the engaged position.

5. The implant insertion device according to claim 1, wherein the first jaw, the second jaw, the third jaw, and the fourth jaw each define a bridge channel, further wherein, when the first jaw, the second jaw, the third jaw, and the fourth jaw reside in the engaged position, each bridge channel is adapted to receive therein a portion of a bridge of the shape memory implant.

6. The implant insertion device according to claim 1, wherein the first jaw, the second jaw, the third jaw, and the fourth jaw each include a leg interface, further wherein, when the first jaw, the second jaw, the third jaw, and the fourth jaw reside in the engaged position, the leg interface of the first jaw and the leg interface of the third jaw are each adapted to engage a first leg of the shape memory implant, the leg interface of the second jaw is adapted to engage a second leg of the shape memory implant, and the leg interface of the fourth jaw is adapted to engage a third leg of the shape memory implant such that the first jaw, the second jaw, the third jaw, and the fourth jaw are adapted to maintain the shape memory implant in the insertion shape.

7. The implant insertion device according to claim 1, wherein the first jaw, the second jaw, the third jaw, and the fourth jaw each include a leg interface, further wherein, when the first jaw, the second jaw, the third jaw, and the fourth jaw reside in the engaged position, the leg interface of the first jaw is adapted to engage a first leg of the shape memory implant, the leg interface of the second jaw is adapted to engage a second leg of the shape memory implant, the leg interface of the third jaw is adapted to engage a third leg of the shape memory implant, and the leg interface of the fourth jaw is adapted to engage a fourth leg of the shape memory implant such that the first jaw, the second jaw, the third jaw, and the fourth jaw are adapted to maintain the shape memory implant in the insertion shape.

8. The implant insertion device according to claim 3, wherein:
   the alignment interfaces of the first jaw and the second jaw each include a leading edge and a trailing edge, whereby, when the first arm, the second arm, the third arm, and the fourth arm reside in the splayed open position, the leading edge of the alignment interface of the first jaw substantially aligns with the trailing edge of the alignment interface of the second jaw such that the leading edge of the alignment interface of the first jaw is located in a plane offset relative to a plane of the leading edge of the alignment interface of the second jaw; and
   the alignment interfaces of the third jaw and the fourth jaw each include a leading edge and a trailing edge, whereby, when the first arm, the second arm, the third arm, and the fourth arm reside in the splayed open position, the leading edge of the alignment interface of the third jaw substantially aligns with the trailing edge of the alignment interface of the fourth jaw such that the leading edge of the alignment interface of the third jaw is located in a plane offset relative to a plane of the leading edge of the alignment interface of the fourth jaw.

9. The implant insertion device according to claim 1, wherein the first jaw, the second jaw, the third jaw, and the fourth jaw each include a slider guide, whereby, when the first jaw, the second jaw, the third jaw, and the fourth jaw reside in the engaged position, the slider guide of the first jaw and the slider guide of the second jaw align and the slider guide of the third jaw and the slider guide of the fourth jaw align such that the slider in the clasped position resides over each slider guides thereby maintaining the first jaw, the second jaw, the third jaw, and the fourth jaw in the engaged position.

10. The implant insertion device according to claim 3, wherein, after delivery of the shape memory implant into the tissue or bone and movement of the slider from the clasped position to the unclasped position, the first arm, the second arm, the third arm, and the fourth arm return from the closed position to the splayed open position resulting in the first jaw, the second jaw, the third jaw, and the fourth jaw progressing from the engaged position to the disengaged position such that the implant insertion device is adapted to release the shape memory implant which attempts to move from the insertion shape to the unconstrained shape, thereby releasing mechanical energy into the tissue or bone.

11. An implant insertion device adapted for use with a shape memory implant movable between an unconstrained shape and an insertion shape, wherein the shape memory implant comprises a bridge interconnecting a first leg, a second leg, and a third leg, further wherein the first leg, the second leg, and the third leg are non-parallel when the shape memory implant resides in the unconstrained shape, and the first leg, the second leg, and the third leg are substantially parallel when the shape memory implant resides in the insertion shape, whereby the implant insertion device maintains the shape memory implant in the insertion shape until a delivery of the shape memory implant into tissue or bone, the implant insertion device, comprising:
 a body, comprising:
  a first jaw including a leg interface,
  a second jaw including a leg interface,
  a third jaw including a leg interface, and
  a fourth jaw including a leg interface, wherein the first jaw, the second jaw, the third jaw, and the fourth jaw are movable from a disengaged position to an engaged position;
 a slider coupled with the body, wherein the slider is movable between an unclasped position and a clasped position, further wherein the slider in the clasped position maintains the first jaw, the second jaw, the third jaw, and the fourth jaw in the engaged position;
 the first jaw resides in opposed relationship with the second jaw, the first jaw and the second jaw including alignment interfaces having complementary angled faces, whereby progression of the first jaw and the second jaw from the disengaged position to the engaged position moves the alignment interfaces into an abutting relationship, further whereby the alignment interfaces due to the complementary angled faces move the first jaw and the second jaw in opposing linear directions such that the leg interface of the first jaw is adapted to engage the first leg of the shape memory implant and the leg interface of the second jaw is adapted to engage the second leg of the shape memory implant to maintain the first leg and the second leg substantially parallel; and the third jaw resides in opposed relationship with the fourth jaw, the third jaw and the fourth jaw including alignment interfaces having complementary angled faces, whereby progression of the third jaw and the fourth jaw to the engaged position moves the alignment interfaces into an abutting relationship, further whereby the alignment interfaces due to the complementary angled faces move the third jaw and the fourth jaw in opposing linear directions such that the leg interface of the third jaw is adapted to engage the first leg of the shape memory implant and the leg interface of the fourth jaw is adapted to engage the third leg of the shape memory implant to maintain the first leg and the third leg substantially parallel.

12. The implant insertion device according to claim 11, wherein the first jaw, the second jaw, the third jaw, and the fourth jaw each define a bridge channel, further wherein, when the first jaw, the second jaw, the third jaw, and the fourth jaw reside in the engaged position, each bridge channel is adapted to receive therein a portion of the bridge of the shape memory implant.

13. The implant insertion device according to claim 11, wherein the body, further comprises:
 a first arm, wherein the first jaw resides at the termination of the first arm;
 a second arm, wherein the second jaw resides at the termination of the second arm;
 a third arm, wherein the third jaw resides at the termination of the third arm; and
 a fourth arm, wherein the fourth jaw resides at the termination of the fourth arm.

14. The implant insertion device according to claim 13, wherein the first arm, the second arm, the third arm, and the fourth arm include a splayed open position that spreads apart the first jaw, the second jaw, the third jaw, and the fourth jaw in the disengaged position, further wherein the first arm, the second arm, the third arm, and the fourth arm are movable from the splayed open position to a closed position that places the first jaw, the second jaw, the third jaw, and the fourth jaw in the engaged position.

15. The implant insertion device according to claim 14 wherein, when the first arm, the second arm, the third arm, and the fourth arm move from the splayed open position to the closed position, the first arm, the second arm, the third arm, and the fourth arm travel along an arc toward a central axis of the body such that the first jaw, the second jaw, the third jaw, and the fourth jaw move angularly to the engaged position.

16. The implant insertion device according to claim 11, wherein the first jaw, the second jaw, the third jaw, and the fourth jaw each include a slider guide, whereby, when the first jaw, the second jaw, the third jaw, and the fourth jaw reside in the engaged position, the slider guide of the first jaw and the slider guide of the second jaw align and the slider guide of the third jaw and the slider guide of the fourth jaw align such that the slider in the clasped position resides over each slider guide thereby maintaining the first jaw, the second jaw, the third jaw, and the fourth jaw in the engaged position.

17. The implant insertion device according to claim 14, wherein, after delivery of the shape memory implant into the tissue or bone and movement of the slider from the clasped position to the unclasped position, the first arm, the second arm, the third arm, and the fourth arm return from the closed position to the splayed open position resulting in the first jaw, the second jaw, the third jaw, and the fourth jaw progressing from the engaged position to the disengaged position such that the implant insertion device is adapted to release the shape memory implant which attempts to move from the insertion shape to the unconstrained shape, thereby releasing mechanical energy into the tissue or bone.

\* \* \* \* \*